(12) United States Patent
Ziv et al.

(10) Patent No.: US 9,198,748 B2
(45) Date of Patent: Dec. 1, 2015

(54) ADJUSTABLE TENSION RING FOR AMELIORATION OF URINARY INCONTINENCE IN FEMALES

(75) Inventors: Elan Ziv, Ramat-Gan (IL); Amir Perle, Haifa (IL); Idan Bauder, Carmiel (IL); Jonathan Bar-Or, Kibbutz Degania Alef Doar-Na Emek HaYarden (IL)

(73) Assignee: ConTIPI Medical Ltd., Caesarea (IL)

(*) Notice: Subject to any disclaimer, the term of this patent is extended or adjusted under 35 U.S.C. 154(b) by 1138 days.

(21) Appl. No.: 12/663,714

(22) PCT Filed: Jun. 11, 2008

(86) PCT No.: PCT/IL2008/000786
§ 371 (c)(1),
(2), (4) Date: Jul. 26, 2010

(87) PCT Pub. No.: WO2008/152628
PCT Pub. Date: Dec. 18, 2008

(65) Prior Publication Data
US 2011/0065980 A1 Mar. 17, 2011

Related U.S. Application Data

(60) Provisional application No. 61/071,344, filed on Apr. 23, 2008, provisional application No. 60/929,063, filed on Jun. 11, 2007.

(51) Int. Cl.
*A61F 2/04* (2013.01)
*A61F 2/00* (2006.01)

(52) U.S. Cl.
CPC .......... *A61F 2/005* (2013.01); *A61F 2250/0001* (2013.01); *A61F 2250/009* (2013.01); *A61F 2250/0012* (2013.01)

(58) Field of Classification Search
CPC ..... A61F 2/0036; A61F 2/005; A61F 2/0009; A61F 2/04; A61F 2250/0007; A61F 2250/0031; A61F 2002/047; A61F 2/004; A61F 6/08; A61B 2017/00805
USPC .......................... 600/29–32, 37; 128/834, 885
See application file for complete search history.

(56) References Cited

U.S. PATENT DOCUMENTS 2,141,040 A 12/1938 Holt
2,146,574 A 2/1939 Hay
(Continued)

FOREIGN PATENT DOCUMENTS

DE 271657 3/1914
DE 19816349 10/1999
(Continued)

OTHER PUBLICATIONS

Response Dated Jun. 5, 2011 to the Communication Pursuant to Article 94(3) EPC of Feb. 4, 2011 From the European Patent Office Re. Application No. 04734069.0.
(Continued)

*Primary Examiner* — Christine H Matthews

(57) ABSTRACT

An apparatus for amelioration of incontinence in a female subject. The apparatus comprises a stiffenable ring adapted for intra-vaginal insertion and a stabilizing extension, projecting axially from the stiffenable ring, the stabilizing extension having a size and position configured to stabilize the stiffenable ring within the vagina.

9 Claims, 13 Drawing Sheets

(56) References Cited

U.S. PATENT DOCUMENTS

| | | | |
|---|---|---|---|
| 2,432,768 A | | 12/1947 | Kurkjian |
| 2,769,442 A | * | 11/1956 | Stubbs .......................... 128/836 |
| 2,856,920 A | * | 10/1958 | Indelicato ..................... 128/836 |
| 2,938,519 A | | 5/1960 | Marco |
| 3,138,159 A | | 6/1964 | Schmidt |
| 3,646,929 A | | 3/1972 | Bonnar |
| 3,658,057 A | * | 4/1972 | Cimber .......................... 128/836 |
| 3,683,906 A | | 8/1972 | Robinson |
| 3,789,828 A | | 2/1974 | Schulte |
| 3,797,478 A | | 3/1974 | Walsh et al. |
| 3,841,304 A | | 10/1974 | Jones |
| 4,019,498 A | | 4/1977 | Hawtrey |
| 4,019,499 A | | 4/1977 | Fitzgerald |
| 4,139,006 A | | 2/1979 | Corey |
| 4,142,649 A | | 3/1979 | Forgey |
| 4,212,301 A | | 7/1980 | Johnson |
| 4,307,716 A | | 12/1981 | Davis |
| 4,428,365 A | | 1/1984 | Hakky |
| 4,457,299 A | | 7/1984 | Cornwell |
| 4,553,533 A | | 11/1985 | Leighton |
| 4,726,805 A | | 2/1988 | Sanders |
| 4,823,814 A | | 4/1989 | Drogendijk et al. |
| 4,846,784 A | | 7/1989 | Haber |
| 4,850,963 A | | 7/1989 | Sparks et al. |
| 4,920,986 A | | 5/1990 | Biswas |
| 5,007,894 A | | 4/1991 | Enhorning |
| 5,014,722 A | | 5/1991 | Bauer |
| 5,036,867 A | | 8/1991 | Biswas |
| 5,041,077 A | * | 8/1991 | Kulick ............................ 600/29 |
| 5,090,424 A | | 2/1992 | Simon et al. |
| 5,167,237 A | * | 12/1992 | Rabin et al. .................... 600/561 |
| 5,224,493 A | | 7/1993 | Sawan et al. |
| 5,224,494 A | | 7/1993 | Enhorning |
| 5,336,208 A | | 8/1994 | Rosenbluth et al. |
| 5,352,182 A | | 10/1994 | Kalb et al. |
| 5,370,657 A | | 12/1994 | Irie |
| 5,386,836 A | | 2/1995 | Biswas |
| 5,417,226 A | | 5/1995 | Juma |
| 5,483,976 A | | 1/1996 | McLaughlin et al. |
| 5,603,685 A | | 2/1997 | Tutrone, Jr. |
| 5,609,586 A | | 3/1997 | Zadini et al. |
| 5,618,256 A | | 4/1997 | Reimer |
| 5,659,934 A | | 8/1997 | Jessup et al. |
| 5,671,755 A | | 9/1997 | Simon et al. |
| 5,724,994 A | | 3/1998 | Simon et al. |
| 5,755,906 A | | 5/1998 | Achter et al. |
| 5,771,899 A | | 6/1998 | Martelly et al. |
| 5,782,745 A | | 7/1998 | Benderev |
| 5,785,640 A | | 7/1998 | Kresch |
| 5,788,664 A | | 8/1998 | Scalise |
| 5,795,346 A | | 8/1998 | Achter et al. |
| 5,894,842 A | | 4/1999 | Rabin et al. |
| 6,013,023 A | | 1/2000 | Klingenstein |
| 6,090,038 A | | 7/2000 | Zunker et al. |
| 6,090,098 A | | 7/2000 | Zunker et al. |
| 6,142,928 A | | 11/2000 | Zunker et al. |
| 6,158,435 A | | 12/2000 | Dorsey |
| 6,189,535 B1 | | 2/2001 | Enhorning |
| 6,216,698 B1 | | 4/2001 | Regula |
| 6,251,122 B1 | | 6/2001 | Tsukernik |
| 6,413,206 B2 | | 7/2002 | Biswas |
| 6,415,484 B1 | | 7/2002 | Moser |
| 6,418,930 B1 | | 7/2002 | Fowler |
| 6,428,467 B1 | | 8/2002 | Benderev |
| 6,458,072 B1 | | 10/2002 | Zunker |
| 6,460,542 B1 | | 10/2002 | James |
| 6,461,215 B1 | | 10/2002 | Kunz et al. |
| 6,478,726 B1 | | 11/2002 | Zunker |
| 6,503,190 B1 | | 1/2003 | Ulmsten et al. |
| 6,558,370 B2 | | 5/2003 | Moser |
| 6,645,136 B1 | | 11/2003 | Zunker et al. |
| 6,676,594 B1 | | 1/2004 | Zunker et al. |
| 6,679,831 B1 | | 1/2004 | Zunker et al. |
| 6,739,340 B1 | | 5/2004 | Jensen et al. |
| 6,770,025 B2 | | 8/2004 | Zunker |
| 6,808,485 B2 | | 10/2004 | Zunker |
| 7,036,511 B2 | | 5/2006 | Nissenkorn |
| 7,717,892 B2 | | 5/2010 | Bartning et al. |
| 7,931,671 B2 | | 4/2011 | Tenerz |
| 8,435,168 B2 | | 5/2013 | Ziv et al. |
| 2002/0068023 A1 | | 6/2002 | Davis |
| 2002/0083949 A1 | | 7/2002 | James |
| 2002/0115906 A1 | * | 8/2002 | Miller ............................. 600/31 |
| 2002/0120243 A1 | | 8/2002 | Kraemer et al. |
| 2002/0138035 A1 | | 9/2002 | Hull, Jr. |
| 2002/0183711 A1 | | 12/2002 | Moser |
| 2003/0073880 A1 | * | 4/2003 | Polsky et al. ................... 600/30 |
| 2003/0149334 A1 | | 8/2003 | Ulmsten et al. |
| 2003/0149392 A1 | | 8/2003 | Arnould |
| 2004/0054252 A1 | | 3/2004 | Zunker |
| 2004/0078013 A1 | | 4/2004 | Zunker et al. |
| 2004/0084054 A1 | | 5/2004 | Kaseki et al. |
| 2004/0122285 A1 | | 6/2004 | Zunker |
| 2004/0158122 A1 | | 8/2004 | Guerquin |
| 2004/0199100 A1 | | 10/2004 | LeMay et al. |
| 2005/0016545 A1 | * | 1/2005 | Nissenkorn ................... 128/834 |
| 2006/0100475 A1 | | 5/2006 | White et al. |
| 2007/0088189 A1 | | 4/2007 | Levy |
| 2007/0203429 A1 | | 8/2007 | Ziv |
| 2007/0244352 A1 | | 10/2007 | Ziv |
| 2008/0149109 A1 | | 6/2008 | Ziv |
| 2008/0281149 A1 | | 11/2008 | Sinai et al. |
| 2009/0266367 A1 | | 10/2009 | Ziv et al. |
| 2009/0283099 A1 | | 11/2009 | Harmanli |
| 2012/0271098 A1 | | 10/2012 | Ziv et al. |
| 2013/0165743 A1 | | 6/2013 | Ziv et al. |
| 2014/0039245 A1 | | 2/2014 | Ziv |
| 2014/0073846 A1 | | 3/2014 | Sinai et al. |
| 2014/0158138 A1 | | 6/2014 | Ziv et al. |

FOREIGN PATENT DOCUMENTS

| | | |
|---|---|---|
| EP | 0264258 | 4/1988 |
| EP | 0274762 | 7/1988 |
| EP | 0933069 | 8/1988 |
| EP | 0700669 | 3/1996 |
| EP | 0921778 | 6/1999 |
| EP | 0955024 | 11/1999 |
| EP | 1139963 | 10/2001 |
| EP | 1139962 | 5/2005 |
| EP | 1727491 | 12/2006 |
| FR | 2843700 | 2/2004 |
| GB | 1115727 | 5/1968 |
| GB | 2352181 | 1/2001 |
| GB | 2384436 | 7/2003 |
| JP | 63-177852 | 7/1988 |
| JP | 03-500489 | 2/1991 |
| JP | 06-133996 | 5/1994 |
| JP | 06-503982 | 5/1994 |
| JP | 61-33996 | 5/1994 |
| JP | 09-501595 | 2/1997 |
| JP | 2001-502929 | 3/2001 |
| JP | 2002-532198 | 2/2002 |
| JP | 2002-5332199 | 10/2002 |
| WO | WO 88/10106 | 12/1988 |
| WO | WO 89/09582 | 10/1989 |
| WO | WO 95/05790 | 3/1995 |
| WO | WO 96/01084 | 1/1996 |
| WO | WO 97/34550 | 9/1997 |
| WO | WO 98/49980 | 11/1998 |
| WO | WO 00/03659 | 1/2000 |
| WO | WO 00/36996 | 6/2000 |
| WO | WO 00/67662 | 11/2000 |
| WO | WO 02/26160 | 4/2002 |
| WO | WO 02/089704 | 11/2002 |
| WO | WO 03/047476 | 6/2003 |
| WO | WO 04/000433 | 12/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |

(56) References Cited

FOREIGN PATENT DOCUMENTS

| WO | WO 2008/152628 | 12/2008 |
|----|----------------|---------|
| WO | WO 2009/044394 | 4/2009  |
| WO | WO 2009/130702 | 10/2009 |

OTHER PUBLICATIONS

Response Dated Aug. 7, 2011 to Office Action of Apr. 5, 2011 From the Israel Patent Office Re.: Application No. 156070.
Response Dated Aug. 10, 2011 to Official Action of May 31, 2011 From the US Patent and Trademark Office Re. U.S. Appl. No. 12/417,011.
Requisition by the Examiner Dated Aug. 22, 2012 From the Canadian Intellectual Property Office Re. Application No. 2,600,988.
Response Dated Aug. 30, 2010 to Notification of Reasons for Rejection of Jun. 1, 2010 From the Japanese Patent Office Re. Application No. 2006-531002.
Requisition by the Examiner Dated Aug. 29, 2011 From the Canadian Intellectual Property Office Re. Application No. 2,560,877.
Official Action Dated Oct. 14, 2011 From the US Patent and Trademark Office Re. U.S. Appl. No. 12/417,011.
Communication Pursuant to Article 94(3) EPC Dated Nov. 3, 2011 From the European Patent Office Re. Application No. 07789949.0.
Examiner's Report Dated Dec. 9, 2009 From the Australian Government, IP Australia Re.: Application No. 2005221424.
International Preliminary Report on Patentability Dated Dec. 23, 2009 From the International Bureau of WIPO Re.: Application No. PCT/IL2008/000786.
International Search Report and the Written Opinion Dated Oct. 28, 2009 From the International Searching Authority Re.: Application No. PCT/IL2009/000443.
Letter After Telephone Conference Dated Jul. 5, 2010 From the International Searching Authority Re. Application No. PCT/IL2009/000443.
Notice of Allowance Dated Mar. 31, 2010 From the US Patent and Trademark Office Re.: U.S. Appl. No. 10/557,865.
Office Action Dated Jan. 18, 2010 From the Israel Patent Office Re.: Application No. 156070 and Its Translation Into English.
Official Action Dated Feb. 19, 2010 From the US Patent and Trademark Office Re.: U.S. Appl. No. 10/593,367.
Response Dated Mar. 15, 2010 to Official Action of Oct. 15, 2009 From the US Patent and Trademark Office Re.: U.S. Appl. No. 10/557,865.
Response Dated Feb. 22, 2010 to International Search Report and the Written Opinion of Oct. 28, 2009 From the International Searching Authority Re.: Application No. PCT/IL2009/000443.
Response Dated Mar. 25, 2010 to Official Action of Feb. 19, 2010 From the US Patent and Trademark Office Re.: U.S. Appl. No. 10/593,367.
Response Dated Dec. 27, 2009 to Official Action of Oct. 29, 2009 From the Federal Institute of Industrial and Intellectual Property, Patents and Trademarks, ROSPATENT, of the Russian Federation Re.: Application No. 2007138489.
Translation of Office Action Dated Jan. 29, 2010 From the State Intellectual Property Office of the People's Republic of China Re.: Application No. 200680017262.2.
Examination Report Dated Oct. 13, 2011 From the Instituto Mexicano de la Propriedad Industrial Re. Application No. MX/a/2007/011339.
Response Dated Oct. 11, 2011 to Decision for Rejection of Jun. 9, 2011 From the Japanese Patent Office Re. Application No. 2007-503495.
Examination Report Dated Oct. 13, 2010 From the Instituto Mexicano de la Propriedad Industrial Re. Application No. MX/a/2007/011339.
Examiner's Report Dated Dec. 15, 2010 From the Australian Government, IP Australia Re.: Application No. 2005221424.
Examiner's Report Dated Nov. 29, 2010 From the Australian Government, IP Australia Re.: Application No. 2005224158.

Official Action Dated Dec. 28, 2010 From the US Patent and Trademark Office Re.: U.S. Appl. No. 10/593,367.
Response Dated Dec. 8, 2010 to Examiner's Report of Dec. 9, 2009 From the Australian Government, IP Australia Re.: Application No. 2005221424.
Response Dated Nov. 16, 2010 to Office Action of Sep. 17, 2010 From the State Intellectual Property Office of the People's Republic of China Re.: Application No. 200680017262.2.
Response Dated Oct. 20, 2010 to Official Action of Jun. 11, 2010 From the Federal Institute of Industrial and Intellectual Property, Patents and Trademarks, ROSPATENT, of the Russian Federation Re.: Application No. 2010100368.
Response Dated Sep. 30, 2010 to Communication Pursuant to Article 94(3) EPC of Mar. 23, 2010 From the European Patent Office Re.: Application No. 05718876.5.
Translation of Notification of Reasons for Rejection Dated Dec. 24, 2010 From the Japanese Patent Office Re. Application No. 2007-503495.
Translation of Office Action Dated Sep. 17, 2010 From the State Intellectual Property Office of the People's Republic of China Re.: Application No. 200680017262.2.
Response Dated Jan. 12, 2011 to Examination Report of Oct. 13, 2010 From the Instituto Mexicano de la Propriedad Industrial Re. Application No. MX/a/2007/011339.
Response Dated Jan. 13, 2011 to Official Action of Oct. 12, 2010 From the US Patent and Trademark Office Re.: U.S. Appl. No. 10/598,872.
Examination Report Dated Oct. 13, 2010 From the Instituto Mexicano de la Propiedad Industrial Re. Application No. MX/a/2007/011339 and Its Summary in English.
Examination Report Dated Oct. 13, 2011 From the Instituto Mexicano de la Propicdad Industrial Re. Application No. MX/a/2007/011339 and Its translation Into English.
Notice of Allowance Dated Jan. 7, 2013 From the US Patent and Trademark Office Re. U.S. Appl. No. 12/373,937.
Office Action Dated Dec. 5, 2012 From the Israel Patent Office Re. Application No. 176883 and Its Translation Into English.
Notice of Acceptance Dated Feb. 2, 2011 From the Australian Government, IP Australia Re.: Application No. 2005221424.
Examination Report Dated Jan. 16, 2012 From the Instituto Mexicano de la Propriedad Industrial Re. Application No. PA/a/2006/010653 and Its Summary in English.
Official Action Dated Feb. 15, 2012 From the US Patent and Trademark Office Re. U.S. Appl. No. 12/373,937.
Official Action Dated Feb. 9, 2011 From the US Patent and Trademark Office Re.: U.S. Appl. No. 10/593,367.
Response Dated Mar. 28, 2011 to Official Action of Dec. 28, 2010 From the US Patent and Trademark Office Re.: U.S. Appl. No. 10/593,367.
Translation of Notification of Reasons for Rejection Dated Mar. 18, 2011 From the Japanese Patent Office Re. Application No. 2006-531002.
Translation of Notification of Reasons of Rejection Dated Apr. 8, 2010 From the Japanese Patent Office Re.: Application No. 2007-503494.
Office Action Dated Apr. 5, 2011 From the Israel Patent Office Re.: Application No. 156070 and Its Translation Into English.
Response Dated Mar. 10, 2011 to Notification of Reasons for Rejection of Dec. 24, 2010 From the Japanese Patent Office Re. Application No. 2007-503495.
International Search Report and the Written Opinion Dated May 9, 2011 From the International Searching Authority Re. Application No. PCT/IL2010/000985.
Translation of Office Action Dated Apr. 29, 2011 From the State Intellectual Property Office of the People's Republic of China Re.: Application No. 200680017262.2.
Communication Pursuant to Article 94(3) EPC Dated Mar. 23, 2010 From the European Patent Office Re.: Application No. 05718876.5.
Requisition by the Examiner Dated May 22, 2012 From the Canadian Intellectual Property Office Re. Application No. 2,560,877.
Communication Under Rule 71(3) EPC Dated May 27, 2011 From the European Patent Office Re. Application No. 09735573.9.

(56) References Cited

OTHER PUBLICATIONS

Official Action Dated May 31, 2011 From the US Patent and Trademark Office Re. U.S. Appl. No. 12/417,011.
International Preliminary Report on Patentability Dated Jun. 7, 2012 From the International Bureau of WIPO Re. Application No. PCT/IL2010/000985.
Official Action Dated Jun. 23, 2010 From the US Patent and Trademark Office Re.: U.S. Appl. No. 10/593,367.
Second Supplemental Notice of Allowability Dated Jun. 3, 2010 From the US Patent and Trademark Office Re.: U.S. Appl. No. 10/557,865.
Reponse Dated Jun. 29, 2010 to Official Action of Apr. 29, 2010 From the US Patent and Trademark Office Re.: U.S. Appl. No. 10/598,872.
Official Action Dated Jun. 11, 2010 From the Federal Institute of Industrial and Intellectual Property, Patents and Trademarks, ROSPATENT, of the Russian Federation Re.: Application No. 2010100368 and Its Summary Into English.
Examination Report Dated May 30, 2012 From the Instituto Mexican de la Propiedad Industrial Re. Application No. MX/a/2007/011339 and Its Translation Into English.
Communiction Pursuant to Article 94(3) EPC Dated Jul. 2, 2010 From the European Patent Office Re.: Application No. 05718877.3.
International Preliminary Report on Patentability Dated Jul. 15, 2010 From the International Preliminary Examining Authority Re.: Application No. PCT/IL2009/000443.
Official Action Dated Jul. 23, 2012 From the US Patent and Trademark Office Re. U.S. Appl. No. 12/373,937.
Official Action Dated Aug. 4, 2010 From the US Patent and Trademark Office Re.: U.S. Appl. No. 10/598,872.
Response Dated Aug. 1, 2010 to Notification of Reasons of Rejection Dated Apr. 8, 2010 From the Japanese Patent Office Re.: Application No. 2007-503494.
Response Dated Aug. 11, 2011 to Examination Report of Mar. 31, 2011 From the Instituto Mexicano de la Propriedad Industrial Re. Application No. MX/a/2007/011339.
Patent Examination Report Dated Aug. 9, 2012 From the Australian Government, IP Australia Re. Application No. 2007274574.
Official Action Dated Aug. 24, 2012 From the US Patent and Trademark Office Re. U.S. Appl. No. 11/886,248.
Response Dated Aug. 31, 2010 to Official Action of Aug. 4, 2010 From the US Patent and Trademark Office Re.: U.S. Appl. No. 10/598,872.
Official Action Dated Oct. 12, 2010 From the US Patent and Trademark Office Re.: U.S. Appl. No. 10/598,872.
Response Dated Oct. 25, 2010 to Official Action of Jun. 23, 2010 From the US Patent and Trademark Office Re.: U.S. Appl. No. 10/593,367.
Response Dated Oct. 19, 2011 to Official Action of Jun. 21, 2011 From the US Patent and Trademark Office Re.: U.S. Appl. No. 10/593,367.
Response Dated Nov. 21, 2011 to Examiner's Report of Nov. 29, 2010 From the Australian Government, IP Australia Re. Application No. 2006224158.
Notice of Allowance Dated Nov. 14, 2011 From the US Patent and Trademark Office Re.: U.S. Appl. No. 10/593,367.
Translation of Office Action Dated Nov. 22, 2012 From the State Intellectual Property Office of the People's Republic of China Re. Application No. 200780033622.2.
Translation of Search Report Dated Nov. 22, 2012 From the State Intellectual Property Office of the People's Republic of China Re. Application No. 200780033622.2.
Response Dated Nov. 3, 2010 to Communication Pursuant to Article 94(3) EPC of Jul. 2, 2010 From the European Patent Office Re. Application No. 057188877.3.
Response Dated Jan. 17, 2011 to Examiner's Report of Dec. 15, 2010 From the Australian Government, IP Australia Re.: Application No. 2005221424.
Restriction Official Action Dated Feb. 28, 2012 From the US Patent and Trademark Office Re. U.S. Appl. No. 11/886,248.

Decision to Refuse a European Patent Application Dated Feb. 25, 2013 From the European Patent Office Re. Application No. 04734069.0.
Requisition by the Examiner Dated Feb. 19, 2013 From the Canadian Intellectual Property Office Re. Application No. 2,560,877.
Communication Pursuant to Article 94(3) EPC Dated Feb. 4, 2011 From the European Patent Office Re. Application No. 04734069.0.
Communication Relating to the Results of the Partial International Search Dated Mar. 3, 2011 From the International Searching Authority Re. Application No. PCT/IL2010/000985.
Notification of Reasons for Rejection Dated Feb. 18, 2011 From the Japanese Patent Office Re. Application No. 2007-503494 and Its Translation into English.
Official Action Dated Feb. 14, 2011 From the US Patent and Trademark Office Re.: U.S. Appl. No. 10/598,872.
Request for Formal Examination Dated Feb. 24, 2011 From the ROSPATENT, Federal Government Institution, Federal Institute of Industrial Property of the Federal Service for Intellectual Property, Patents and Trademarks of the Russian Federation Re. Application No. 2010146714.
Examination Report Dated Feb. 16, 2012 From the Government of India, Patent Office, Intellectual Property Building Re. Application No. 3837/CHENP/2006.
Translation of Office Action Dated Feb. 22, 2012 From the State Intellectual Property Office of the People's Republic of China Re. Application No. 200780033622.2.
Official Action Dated Mar. 12, 2013 From the US Patent and Trademark Office Re. U.S. Appl. No. 12/680,575.
Supplemental Notice of Allowability Dated Apr. 2, 2013 From the US Patent and Trademark Office Re. U.S. Appl. No. 12/373,937.
Translation of Office Action Dated Mar. 5, 2013 From the State Intellectual Property Office of the People's Republic of China Re. Application No. 200980123856.5.
Translation of Reasons for Rejection Dated Mar. 18, 2013 From the Japanese Patent Office Re. Application No. 2011-223943.
Communication Pursuant to Article 94(3) EPC Dated Apr. 16, 2009 From the European Patent Office Re.: Application No. 05718876.5.
Communication Relating to the Results of the Partial International Search Dated Dec. 7, 2007 From the International Searching Authority Re.: Application No. PCT/IL2007/000893.
Communication Relating to the Results of the Partial International Search Dated Jan. 12, 2009 From the International Searching Authority Re.: Application No. PCT/IL2007/000893.
Communication Relating to the Results of the Partial International Search Dated Jan. 12, 2009 From the International Searching Authority Re.: Application No. PCT/IL2008/001292.
Communication Relating to the Results of the Partial International Search Dated Aug. 18, 2009 From the International Searching Authority Re.: Application No. PCT/IL2009/000443.
Communication Under Rule 112 EPC Dated Oct. 22, 2007 From the European Patent Office Re.: Application No. 05718876.5.
Communiction Pursuant to Article 94(3) EPC Dated Apr. 16, 2009 From the European Patent Office Re.: Application No. 05718877.3.
European Search Report Under Rule 112 EPC Dated Dec. 27, 2007 From the European Patent Office Re.: Application No. 05718876.5.
International Preliminary Report on Patentability Dated Jul. 6, 2006 From the International Preliminary Examining Authority Re.: Application No. PCT/IL2005/000304.
International Preliminary Report on Patentability Dated Dec. 8, 2009 From the International Preliminary Examining Authority Re.: Application No. PCT/IL2008/001292.
International Preliminary Report on Patentability Dated Oct. 14, 2008 From the International Preliminary Examining Authority Re.: Application No. PCT/IL06/00346.
International Preliminary Report on Patentability Dated Jul. 24, 2006 From the International Preliminary Examining Authority Re.: Application No. PCT/IL2005/000303.
International Preliminary Report on Patentability Dated Jan. 29, 2009 From the International Bureau of WIPO Re.: Application No. PCT/IL2007/000893.
International Search Report and the Written Opinion Dated Oct. 26, 2005 From the International Searching Authority Re.: Application No. PCT/IL2005/000303.

(56) References Cited

OTHER PUBLICATIONS

International Search Report Dated Dec. 11, 2006 From the International Searching Authority Re.: Application No. PCT/IL06/00346.
International Search Report Dated Apr. 14, 2008 From the International Searching Authority Re.: Application No. PCT/IL2007/000893.
International Search Report Dated Sep. 23, 2005 From the International Searching Authority Re.: Application No. PCT/IL2005/000304.
International Search Report Dated Oct. 24, 2008 From the International Searching Authority Re.: Application No. PCT/IL2008/000786.
International Search Report Dated Mar. 25, 2009 From the International Searching Authority Re.: Application No. PCT/IL2008/001292.
Notification Dated Dec. 17, 2008 From the Patent Office of the Russian Federation Re.: Application No. 2006136791 and Its Translation Into Emglish.
Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Office Action Dated Jan. 9, 2009 From the State Intellectual Property Office of the People's Republic of China Re.: Application No. 200580016245.2 and Its Translation Into English.
Official Action Dated Sep. 5, 2008 From the US Patent and Trademark Office Re.: U.S. Appl. No. 10/557,865.
Official Action Dated Mar. 6, 2009 From the US Patent and Trademark Office Re.: U.S. Appl. No. 10/557,865.
Official Action Dated Oct. 15, 2009 From the US Patent and Trademark Office Re.: U.S. Appl. No. 10/557,865.
Official Action Dated Apr. 17, 2009 From the Patent Office of the Russian Federation Re.: Application No. 2006136791 and Its Translation Into English.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Written Opinion Dated Dec. 11, 2006 From the International Searching Authority Re.: Application No. PCT/IL06/00346.
Written Opinion Dated Apr. 14, 2008 From the International Searching Authority Re.: Application No. PCT/IL2007/000893.
Written Opinion Dated Nov. 22, 2005 From the International Searching Authority Re.: Application No. PCT/IL2004/000433.
Written Opinion Dated May 23, 2006 From the International Preliminary Examining Authority Re.: Application No. PCT/IL2005/000303.
Written Opinion Dated Sep. 23, 2005 From the International Searching Authority Re.: Application No. PCT/IL2005/000304.
Written Opinion Dated Oct. 24, 2008 From the International Searching Authority Re.: Application No. PCT/IL2008/000786.
Written Opinion Dated Mar. 25, 2009 From the International Searching Authority Re.: Application No. PCT/IL2008/001292.
Examination Report Dated Mar. 31, 2011 From the Instituto Mexicano de la Propriedad Industrial Re. Application No. MX/a/2007/011339.
Official Action Dated Apr. 29, 2010 From the US Patent and Trademark Office Re.: U.S. Appl. No. 10/598,872.
Supplemental Notice of Allowability Dated Apr. 27, 2010 From the US Patent and Trademark Office Re.: U.S. Appl. No. 10/557,865.
Official Action Dated May 6, 2013 From the US Patent and Trademark Office Re. U.S. Appl. No. 11/886,248.
Requisition by the Examiner Dated May 28, 2013 From the Canadian intellectual Property Office Re. Application No. 2,600,988.
Translation of Decision for Rejection Dated Jun. 9, 2011 From the Japanese Patent Office Re. Application No. 2007-503495.
Translation of Notification of Reasons for Rejection Dated Jun. 1, 2010 From the Japanese Patent Office Re. Application No. 2006-531002.

Response Dated Jun. 21, 2010 to Office Action of Jan. 29, 2010 From the State Intellectual Property Office of the People's Republic of China Re.: Application No. 200680017262.2.
Response Dated Jun. 1, 2011 to Notification of Reasons for Rejection of Mar. 18, 2011 From the Japanese Patent Office Re. Application No. 2006-531002.
Response Dated Jun. 14, 2011 to Official Action of Feb. 14, 2011 From the US Patent and Trademark Office Re.: U.S. Appl. No. 10/598,872.
Response Dated May 29, 2011 to Communication Pursuant to Article 94(3) EPC of Feb. 4, 2011 From the European Patent Office Re. Application No. 04734069.0.
Official Action Dated Jun. 21, 2011 From the US Patent and Trademark Office Re.: U.S. Appl. No. 10/593,367.
Response Dated Jun. 20, 2011 to Office Action of Dec. 21, 2010 From the State Intellectual Property Office of the People's Republic of China Re. Application No. 200780033622.2.
Translation of Office Action Dated Dec. 21, 2010 From the State Intellectual Property Office of the People's Republic of China Re. Application No. 200780033622.2.
Office Action Dated Jul. 24, 2011 From the Israel Patent Office Re. Application No. 176883 and Its Translation Into English.
Restriction Official Action Dated Nov. 1, 2012 From the US Patent and Trademark Office Re. U.S. Appl. No. 12/680,575.
Examiner-Initiated Interview Summary Dated Oct. 10, 2012 From the US Patent and Trademark Office Re. U.S. Appl. No. 12/680,575.
Communication Pursuant to Rules 70(2) and 70a(2) EPC and Reference to Rule 39(1) EPC Dated Jan. 9, 2012 From the European Patent Office Re. Application No. 11179593.6.
Response Dated Jun. 29, 2011 to Office Action of Apr. 29, 2011 From the State Intellectual Property Office of the People's Republic of China Re.: Application No. 200680017262.2.
Applicant-Initiated Interview Summary Dated Jun. 28, 2013 From the US Patent and Trademark Office Re. U.S. Appl. No. 12/680,575.
Invitation Pursuant to Rule 62a(1) EPC Dated Aug. 8, 2013 From the European Patent Office Re. Application No. 06711327.4.
Notice of Allowance Dated Aug. 6, 2013 From the US Patent and Trademark Office Re. U.S. Appl. No. 11/886,248.
Official Action Dated Jul. 23, 2013 From the US Patent and Trademark Office Re. U.S. Appl. No. 10/598,872.
Applicant-Initiated Interview Summary Dated Aug. 9, 2013 From the US Patent and Trademark Office Re. U.S. Appl. No. 12/680,575.
Translation of Office Action Dated Aug. 22, 2013 From the State Intellectual Property Office of the People's Republic of China Re. Application No. 200780033622.2.
Communication Pursuant to Rules 70(2) and 70a(2) EPC Dated Nov. 8, 2013 From the European Patent Office Re. Application No. 06711327.4.
Notice of Allowance Dated Oct. 2, 2013 From the US Patent and Trademark Office Re. U.S. Appl. No. 12/417,011.
Notification of Reasons for Rejection Dated Oct. 4, 2013 From the Japanese Patent Office Re. Application No. 2011-223943 and Its Translation Into English.
Official Action Dated Sep. 24, 2013 From the US Patent and Trademark Office Re. U.S. Appl. No. 13/772,410.
Supplemental Notice of Allowability Dated Sep. 24, 2013 From the US Patent and Trademark Office Re. U.S. Appl. No. 11/886,248.
Supplementary European Search Report and the European Search Opinion Dated Oct. 21, 2013 From the European Patent Office Re. Application No. 06711327.4.
European Search Report and the European Search Opinion Dated Nov. 14, 2013 From the European Patent Office Re. Application No. 11188150.4.
Applicant-Initiated Interview Summary Dated Jan. 16, 2014 From the US Patent and Trademark Office Re. U.S. Appl. No. 13/772,410.
Communication Pursuant to Rules 70(2) and 70a(2) EPC and Reference to Rule 39(1) EPC Dated Jan. 2, 2014 From the European Patent Office Re. Application No. 11188150.4.
Office Action Dated Dec. 31, 2013 From the Israel Patent Office Re. Application No. 219988 and Its Translation Into English.
Office Action Dated Dec. 31, 2013 From the Israel Patent Office Re. Application No. 222951 and Its Translation Into English.

(56) References Cited

OTHER PUBLICATIONS

Communication Pursuant to Article 94(3) EPC Dated Nov. 29, 2013 From the European Patent Office Re. Application No. 08808093.2.
Office Action Dated Nov. 12, 2013 From the State Intellectual Property Office of the People's Republic of China Re. Application No. 200980123856.5 and Its Translation Into English.
Office Action Dated Dec. 19, 2013 From the Israel Patent Office Re. Application No. 219989 and Its Translation Into English.
Translation of Office Action Dated May 6, 2013 From the State Intellectual Property Office of the People's Republic of China Re. Application No. 200780033622.2.
Office Action Dated May 14, 2014 From the State Intellectual Property Office of the People's Republic of China Re. Application No. 200980123856.5 and Its Translation Into English.
Communication Pursuant to Article 94(3) EPC Dated Jan. 31, 2014 From the European Patent Office Re. Application No. 08763544.7.
Official Action Dated Jan. 27, 2014 From the US Patent and Trademark Office Re. U.S. Appl. No. 12/680,575.
Supplemental Notice of Allowability Dated Mar. 5, 2014 From the US Patent and Trademark Office Re. U.S. Appl. No. 10/598,872.
Invitation Pursuant to Article 94(3) EPC Dated Jun. 17, 2014 From the European Patent Office Re. Application No. 08763544.7.
Communication Pursuant to Article 94(3) EPC Dated Feb. 23, 2015 From the European Patent Office Re. Application No. 08763544.7.
European Search Report Dated Mar. 11, 2015 From the European Patent Office Re. Application No. 14192972.9.
Official Action Dated Apr. 9, 2012 From the US Patent and Trademark Office Re. U.S. Appl. No. 12/417,011.
Request for Examination Dated Mar. 29, 2012 From the Federal Institute of Industrial and Intellectual Property, Patents and Trademarks, ROSPATENT, of the Russian Federation Re.: Application No. 2010100368 and Its Summary in English.
Request for Examination Dated Apr. 4, 2013 From the Federal Service for Intellectual Property, Federal State Budgetary Institution, Federal Institute of Industrial Property of theRussian Federation Re. Application No. 2010146714 and Its Summary in English.

\* cited by examiner

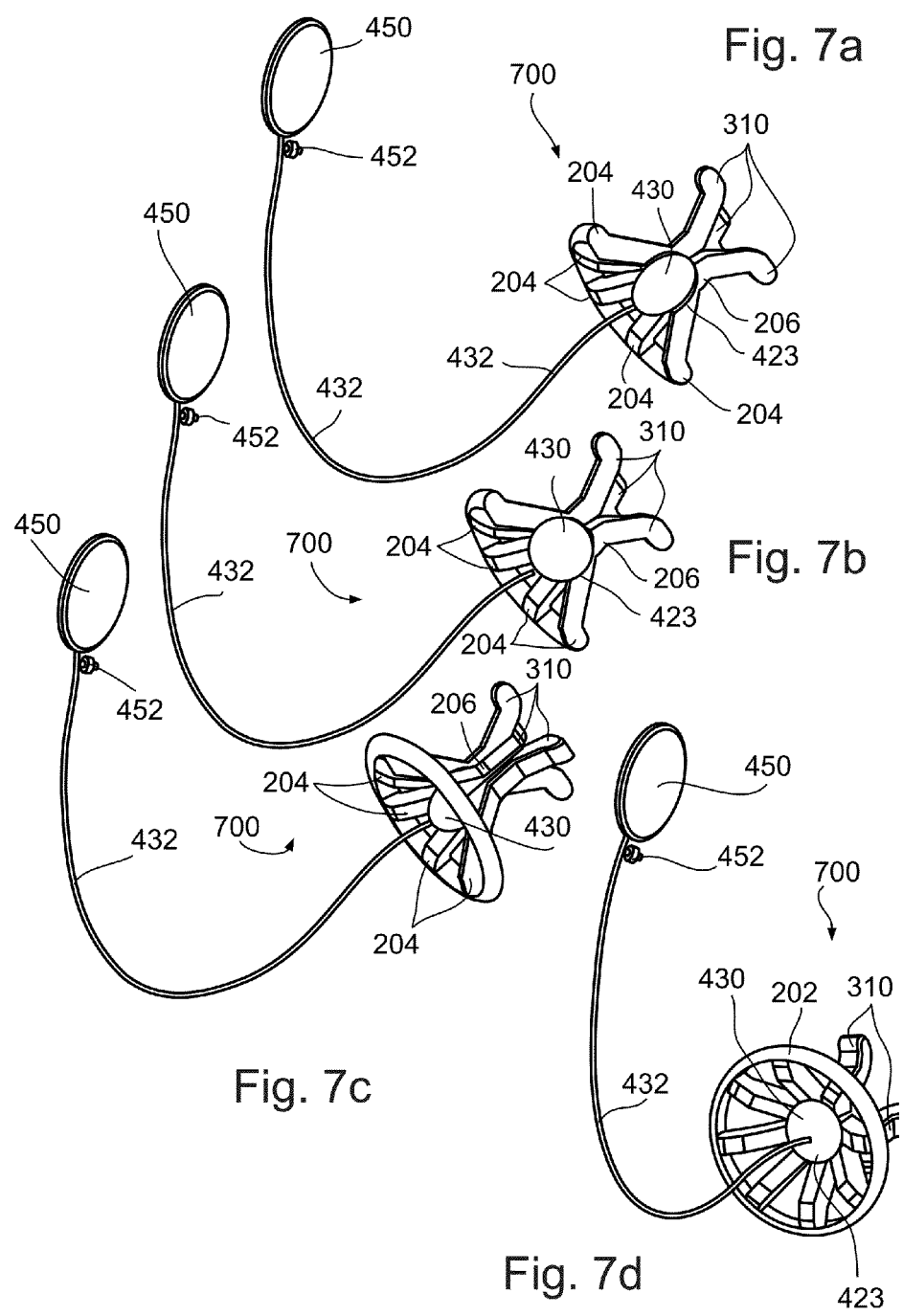

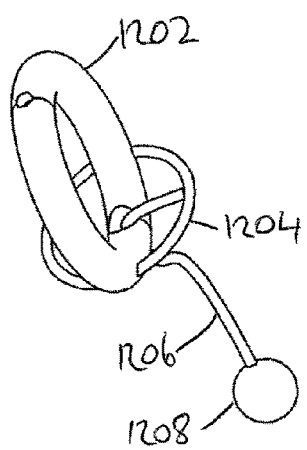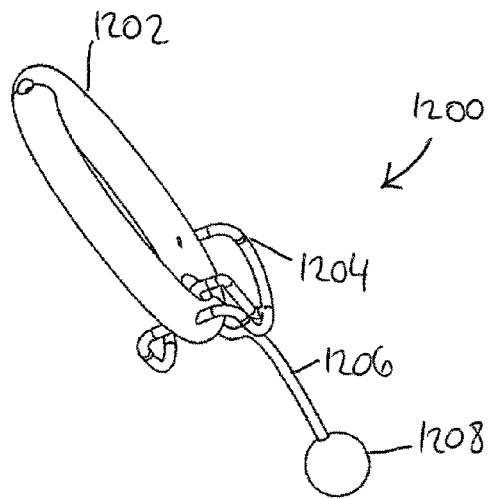
Fig. 12C  Fig. 12A
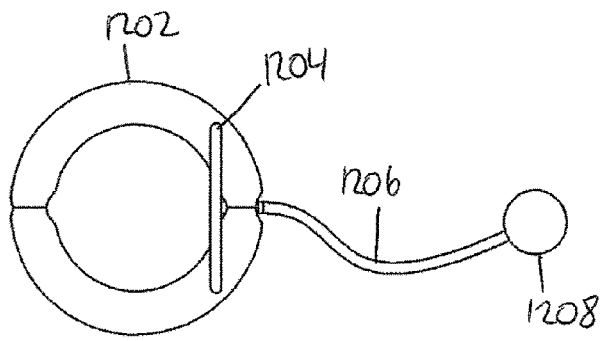
Fig. 12D
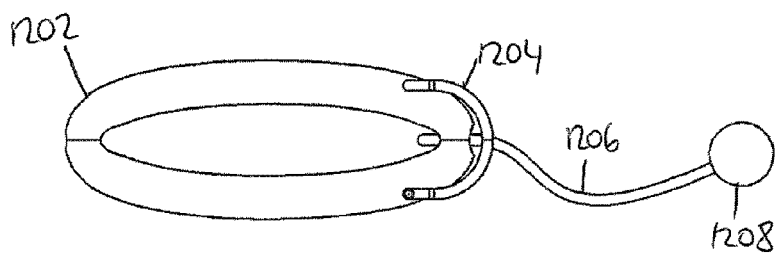
Fig. 12B

ADJUSTABLE TENSION RING FOR AMELIORATION OF URINARY INCONTINENCE IN FEMALES

RELATED APPLICATIONS

This Application is a National Phase of PCT Patent Application No. PCT/IL2008/000786 having International filing date of Jun. 11, 2008, which claims the benefit of priority under 119(e) from U.S. Provisional Patent Application Nos. 61/071,344, filed on Apr. 23, 2008 and 60/929,063, filed on Jun. 11, 2007. The contents of the above Applications are all incorporated herein by reference.

FIELD OF INVENTION

The present invention, in some embodiments thereof, relates to an intra-vaginal device for amelioration of female incontinence and methods of use thereof.

BACKGROUND OF THE INVENTION

Urinary incontinence is a widespread problem among females. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise occurring during exercise, coughing, sneezing, laughing, etc.

While many different factors may contribute to the development of stress incontinence, it is most prevalent among women ages 35-65 and those who have had multiple vaginal deliveries.

Stress incontinence is both aggravating and unpleasant for women, and it can also be embarrassing. Many women wear sanitary pads or diapers in order to deal with incontinence, though this is not a real solution to the problem and it can be very inconvenient and unreliable.

Surgical treatment may involve securing the paraurethal tissues to the periosteum of the pubic bone or the rectus facia, and/or to ligaments on the bony pelvis, in order to elevate the bladder neck above the pelvic floor and thereby distribute pressure equally to the bladder, the bladder neck, and the mid-urethra. Recently, a procedure known as "TVT" ("Tension Free Vaginal Tape") was developed, in which a mesh tape is implanted underneath the mid-urethra, creating a hammock on which the urethra may kink during a rise in intra-abdominal pressure. However, surgery is only suitable for severe cases, and the majority of women experiencing incontinence do not need, and certainly would rather avoid, surgical solutions.

One modality of non-surgical treatment involves the use of devices that are inserted into the vagina, either by a medical practitioner or by the woman herself. Most devices are designed to apply pressure against the bladder neck so as to inhibit or completely block the flow of urine through the urethra.

A variety of such devices are known in the art. For example, refer to U.S. Publication No. 2002/0183711 to Moser, entitled, "Urinary Incontinence Device"; U.S. Pat. No. 6,739,340 to Jensen, et al., entitled, "Device for prevention of involuntary urination"; U.S. Pat. No. 6,679,831 to Zunker, et al., entitled, "Resilient incontinence insert and a method of making the same"; U.S. Pat. No. 6,460,542 to James, entitled, "Female incontinence control device"; U.S. Pat. No. 6,413,206 to Biswas, entitled, "Intra-vaginal device"; U.S. Pat. No. 5,785,640 to Kresch, entitled "Method for Treating Female Incontinence"; U.S. Pat. No. 5,771,899 to Martelly, et al., entitled, "Pessary"; U.S. Pat. No. 5,618,256 to Reimer, entitled, "Device for Arrangement in the Vagina for Prevention of Involuntary Urination with Females and an Applicator for use in Insertion of the Device"; U.S. Pat. No. 5,417,226 to Juma, entitled, "Female Anti-Incontinence Device"; U.S. Pat. No. 5,386,836 to Biswas, entitled, "Urinary Incontinence Device"; U.S. Pat. No. 5,007,894 to Enhorning, entitled, "Female Incontinence Device"; and U.S. Pat. No. 4,920,986 to Biswas, entitled, "Urinary Incontinence Device", the disclosures of which are herein incorporated by reference.

Urge incontinence is characterized by a relatively high pressure in the bladder. Some apparatus well suited for treatment of stress urinary incontinence (e.g. urethral inserts) may completely block the urethra hence may be used for any kind of incontinence, but are not specifically intended for treating urge incontinence. PCT application WO 2005/087154 by Ziv et al. describes apparatus for treatment of incontinence featuring a ring which applies pressure directly to the urethra.

Older people living in long-term care facilities usually have multiple illnesses with functional impairment, including hand-mobility limitations, sensory impairment, slow reactions, some neurological damage, and/or cognitive impairment. Even in patients not wearing diapers, there is often constant wetness with resulting problems, for example, skin problems.

Background art includes the following patent, the content of which is incorporated by reference as if fully set forth herein: GB 1115727; Apparatus Controlling Incontinence in the Female.

SUMMARY OF THE INVENTION

The present invention, in some embodiments thereof, relates to an intra-vaginal device for amelioration of female incontinence and methods of use thereof.

There is provided in accordance with an exemplary embodiment of the invention, an apparatus for amelioration of urinary incontinence in a female subject, the apparatus comprising:

(a) a ring with adjustable stiffness, adapted for intra-vaginal insertion; and (b) a stabilizing projection, extending transversely to a plane of said stiffenable ring, said stabilizing projection having a size, shape, stiffness and position configured to stabilize said stiffenable ring within the vagina.

In an exemplary embodiment of the invention, said stiffenable ring is adapted to switch from a first geometric configuration outside the body to a second configuration after intra vaginal insertion. Optionally, said switch from said first configuration to said second configuration is performed mechanically.

In an exemplary embodiment of the invention, said apparatus includes a tensioning extension adapted to extend outside of the body, said tensioning extension adapted for selectively increasing and decreasing a rigidity of said ring after insertion thereof. Optionally, said apparatus includes a stiffening control. Optionally, said stiffening control is adapted to lock in a plurality of positions. Optionally or alternatively, said stiffening control is adapted for one handed use.

In an exemplary embodiment of the invention, said ring comprises an inner lumen in fluid communication with said tensioning extension and wherein said tensioning extension comprises:

(i) a reservoir of material; and (ii) a transfer element adapted to move at least a portion of the material into said inner lumen of said stiffenable ring. Optionally, said material comprises a liquid. Alternatively, said material comprises a gas.

In an exemplary embodiment of the invention, said reservoir of material comprises an additional length of tubing defining a lumen in fluid communication with said inner lumen of said tubing of said ring.

In an exemplary embodiment of the invention, the transfer element comprises a constricting element axially translatable along said reservoir.

In an exemplary embodiment of the invention, said tensioning element comprises a pull wire adapted to one or both of unfold and tension said ring.

In an exemplary embodiment of the invention, the apparatus comprises at least one arm supporting said ring and at least one tension element that retracts said ring while said arm supports said ring, thereby changing a stiffness in said ring.

In an exemplary embodiment of the invention, said tensioning extension comprises a static state and a second state which is biased to change back to said static state.

In an exemplary embodiment of the invention, said tensioning extension comprises a plurality of at least 3 different stable states corresponding to different stiffness states of said ring.

In an exemplary embodiment of the invention, the apparatus comprises at least one transverse support element engaging said ring.

In an exemplary embodiment of the invention, the apparatus comprises at least one cone shaped skirt covering apart of said device.

In an exemplary embodiment of the invention, said stabilizing extension includes a cone shaped section.

In an exemplary embodiment of the invention, said stabilizing extension comprises an axial stabilizing rod.

In an exemplary embodiment of the invention, said stabilizing extension includes a trans-axial stabilizing element.

In an exemplary embodiment of the invention, said stabilizing extension is configured to stretch a vaginal wall.

In an exemplary embodiment of the invention, said stabilizing extension is configured to at least ameliorate pelvic organ prolapse.

In an exemplary embodiment of the invention, said stabilizing extension is configured to support collapsing of a vaginal wall thereon.

In an exemplary embodiment of the invention, said stabilizing extension is configured to pass vaginal secretions therethrough.

In an exemplary embodiment of the invention, said stabilizing extension comprises an anchor extending axially away from said ring, said anchor adapted for one or more of reducing translational motion, reducing tipping of the ring and/or reducing ring rotation, with respect to a vaginal wall.

In an exemplary embodiment of the invention, the apparatus includes at least one through aperture for flow of vaginal secretions therethrough.

In an exemplary embodiment of the invention, the apparatus is adapted to function in a substantially same manner irrespective of an orientation thereof around an axis of said vagina.

There is provided in accordance with an exemplary embodiment of the invention, a method for ameliorating incontinence, the method comprising:

(a) intra-vaginally inserting a non-space filling tensional element to contact a vaginal wall;

(b) stabilizing said ring in said vagina using at least one axial extension;

(c) selectively increasing and decreasing a pressure applied by said stiffenable ring to the vaginal wall. Optionally, said inserting comprises inserting in an orientation independent manner. Optionally or alternatively, said stiffenable ring is substantially planar. Optionally or alternatively, said stabilizing projection extends along an axis of said stiffenable ring. Optionally or alternatively, said ring applies pressure to a urethra. Optionally or alternatively, a plane of said ring is perpendicular to an axis of the urethra. Optionally or alternatively, the method comprises:

introducing fluid into a lumen of tubing forming said stiffenable ring as a means of achieving said increasing. Optionally, the method comprises:

(d) transferring fluid from additional tubing into said lumen of tubing forming said stiffenable ring as a means of introducing said fluid.

In an exemplary embodiment of the invention, stabilizing comprises anchoring said stiffenable ring to resist translational motion within the vagina. Optionally, said translational motion comprise axial motion.

In an exemplary embodiment of the invention, stabilizing comprises anchoring said stiffenable ring to resist tipping of said ring within the vagina.

In an exemplary embodiment of the invention, the method comprises decreasing a pressure applied by said stiffenable ring to the vaginal wall.

In an exemplary embodiment of the invention, said increasing is performed substantially immediately after intravaginal insertion of said stiffenable ring. Optionally or alternatively, said increasing is performed in response to an anticipated urge. Optionally or alternatively, said increasing is performed in response to an actual urge. Optionally or alternatively, said increasing is for a time period appropriate to reach a bathroom. Optionally or alternatively, said decreasing is performed after an urge passes. Optionally or alternatively, the method comprises removing said stiffenable ring from the vagina. Optionally, said decreasing is performed substantially immediately prior to removal of said stiffenable ring.

In an exemplary embodiment of the invention, said selectively increasing and decreasing is performed by a caregiver.

In an exemplary embodiment of the invention, the method comprises providing prolapse amelioration using said ring, said anchor or both.

In an exemplary embodiment of the invention, said stiffness is adjusted in discrete increments.

In an exemplary embodiment of the invention, said stiffness is adjusted continuous within a range of available stiffness settings.

There is provided in accordance with an exemplary embodiment of the invention, a method of regulating a degree of incontinence control, the method comprising:

(a) providing an intra-vaginal ring having a stabilizing projection, said intra-vaginal ring configured to apply a selected degree of pressure to an organ through a vaginal wall;

(b) varying said pressure responsive to a need for incontinence control.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-7D show an adjustable incontinence device, having an inner inflatable section, according to an exemplary embodiment of the invention;

FIGS. 12A-12D show an adjustable incontinence device, with said second anchoring/stabilizing section design and an alternative tensioning element design, according to an exemplary embodiment of the invention.

DESCRIPTION OF EMBODIMENTS

Figure 1:
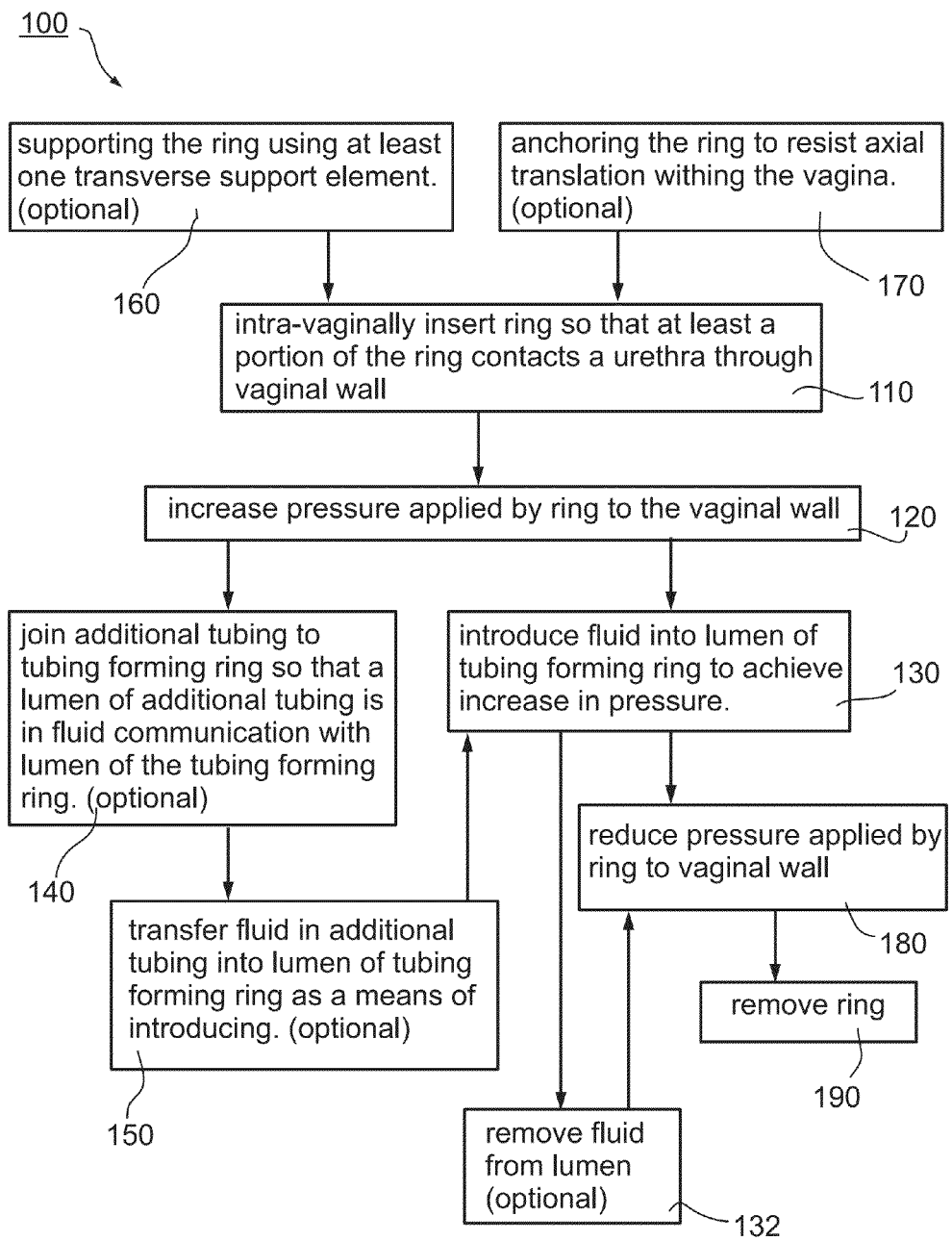
FIG. 1 is a simplified flowchart of a method for management of incontinence according to some embodiments of the invention.

An aspect of some embodiments of the invention relates to device including a stiffenable element adapted for insertion into a vagina.

In an exemplary embodiment of the invention, the device is used for treatment or amelioration of incontinence, for example, one or more of Urge incontinence, Overflow incontinence, Posture related incontinence and/or Neurogenic incontinence. Optionally or alternatively, the device is used for treating or ameliorating pelvic organ prolapse.

In an exemplary embodiment of the invention, the stiffenable elements is a ring shaped element which is selectable stiffenable and/or softenable, so that it applies a different force against a vaginal wall and/or a urethra.

In an exemplary embodiment of the invention, at least one anchoring element is attached to the ring.

In an exemplary embodiment of the invention, the ring is an annular, substantially symmetric (e.g., rotationally symmetric) element that works in a similar manner independent of its rotation. Optionally, the ring defines at least one aperture therethrough. In an exemplary embodiment of the invention, the stiffening of the ring is substantially uniform along its circumference, for example, being within 20% over at least 80% or 90% of its circumference In an exemplary embodiment of the invention, the ring is tensioned in one or more of several manners, including, internal stiffening, for example, by expansion (e.g., using an internal fluid lumen), or by shrinking (e.g., shortening an internal wire), by extension (e.g., using a plurality of internal arms that push ring out), by distortion (e.g., using an element that pulls the ring in a direction perpendicular to its plane and thereby also causing radial extension thereof.

In an exemplary embodiment of the invention, the anchor serves for at least one of axial motion prevention, rotational motion prevention and/or plane tipping. In an exemplary embodiment of the invention, the anchor is substantially perpendicular to a plane of the ring. Optionally, the ring is at a non-perpendicular angle to the anchor, for example, 89, 80, 70, 60, 50, 30, 20 10, 0 degrees or intermediate angles. This angle may affect the mode of operation of the ring.

In an exemplary embodiment of the invention, the anchor acts by friction. Optionally or alternatively, the anchor causes collapse of a vaginal wall thereof. Optionally or alternatively, the anchor stretches the vaginal walls.

Optionally, the anchor is non-deforming, for example, being rod shaped. Optionally or alternatively, the anchor expands, for example, being inflatable (e.g., a balloon) or being self expanding. Optionally, the anchor includes multiple elements which move away form each other as the anchor is deployed.

In an exemplary embodiment of the invention, the anchor is axial with respect to the ring. Optionally, the anchor is connected to the circumference of the ring using a plurality of elongate elements. Optionally or alternatively, the anchor extends from a circumference of the ring or another point intermediate the circumference and the center of the ring. Optionally, non-functional parts of the anchor are not rotationally symmetric, for example, the anchor comprising an L-shaped element that extends from the ring circumferences towards an line along its axis and then continues along that line. A functional part of the anchor may be the axial section. Optionally or alternatively, the anchor is not straight, but includes one or more kinks, hooks and/or extensions, optionally, not symmetrically arranged with respect to the ring axis.

In an exemplary embodiment of the invention, a stiffening control is provided which reaches outside of the vagina and is mechanically operated. Optionally, the control can be activated using one hand and/or two or three fingers of one hand.

In an exemplary embodiment of the invention, the stiffing ring serves as an external sphincter for the urethra to selectable control urination and thus incontinence. Optionally, a safety mechanism is provide to automatically activate and/or deactivate the sphincter effect, for example, to prevent involuntary leakage and/or prevent urine retention. Optionally or alternatively, the ring has a "base" stiffness degree and that stiffness can be varied, wither up or down, depending on need and/or implementation. Optionally, the ring tends to revert back to the base degree. Optionally or alternatively, the stiffening of the ring is cyclical, for example, under electronic control, for example, using a motor which periodically increases and/or decreases stiffness, for example, by mechanically actuating one of the stiffening mechanisms described herein. Such a motor is optionally outside the body.

In an exemplary embodiment of the invention, the size, diameter, softness, contact force, contact cross-section, diameter of ring body and/or angle of ring relative to vagina depend on the desired ring function, for example, direct blockage of urethra, stretching of vaginal walls and/or organ prolapse.

Below are described a variety of exemplary embodiments illustrating ring shapes, tensioning/stiffening mechanisms, anchor shapes and functions and/or other features. It should be appreciated that the scope of the invention includes embodiments that utilize features form different embodiments, utilize overlapping features (e.g., multiple anchor deigns) and/or multiple instances (e.g., multiple inflatable rings for vaginal force application).

In embodiments of the invention, the element is hollow, for example comprising a torus in a stiffened configuration, to allow flow of vaginal secretions therethrough.

Optionally, the element includes a part that does not stiffen or that remains stiffened, for example, an anchor when the stiffenable element is in a soft state and/or in a stiffened configuration. In embodiments, the anchor includes portions that enhance friction against vaginal tissue and associated position stability of the stiffenable element.

Alternatively or additionally, the anchor is designed to position the stiffenable element in a desired position in the vagina. In embodiments of the invention, the stiffenable element is configured so that it applies a same force on the vaginal wall regardless of an insertion and/or seating orientation.

In embodiments of the invention, the stiffenable element is hollow and operates by having a relatively small amount of fluid or other flowable material pushed therein, so that its internal pressure increases and thereby its rigidity increases. Optionally, the stiffenable element is always nearly full and stiffening is accomplished by adding an additional, relatively small, amount of fluid or other flowable material into the hollow.

Optionally, the stiffening element includes a skirt that presses against the vagina, thereby promoting stability of position and/or efficacy of the stiffening element.

In one operational mode, provided in some embodiments of the invention, this stiffenable element contacts the tissue to be treated, for example, a urethra (through the vaginal wall) and/or a bladder neck, and provides support thereto. In another operational mode, provided in some embodiments of the invention, the element contacts and stretches the vaginal walls to achieve a desired effect.

In embodiments of the invention, the stiffenable element is adapted to be selectively stiffened and softened multiple times in a day. In some embodiment, the element has a preferred stiffness state and it returns to that preferred state after a time period without user intervention.

In embodiments of the invention, the stiffening element device is substantially planar, with a maximal extension in one dimension of less than ¼ of those in the other dimensions. Alternatively, the device may be non-planar. Optionally, the anchoring element extends axially from the stiffening element.

In embodiments of the invention, when the stiffenable element comprises an adjustable tension ring deployed intravaginally to ameliorate incontinence, as tension in the ring increases, pressure applied to the urethra increases.

In embodiments of the invention, the ring is constructed of flexible tubing (e.g. Nylon, Silicone, Polyurethane, and Tygon). Optionally, pressure in the ring is increased by forcing a liquid or gas into a lumen of the tubing. Optionally, the ring includes an extension tube and liquid is forced into the lumen of the extension tube by compressing a portion of the extension tubing, for example by sliding a bead along the extension tubing.

Optionally, the stiffenable element is a non-planar shape, for example, in the form multiple intersection (and optionally orthogonal) rings or a space filling helix. Optionally, the anchoring element extends axially from the stiffening element when the stiffening element is in a stiffened configuration.

Optionally, the stiffenable element defines an outer periphery comprising an ellipsoid, rhomboid, or a ball. Optionally, an internal framework, comprising the above-noted anchoring element and/or extensions thereof, is provided to hold this shape. Optionally however, the internal volume of the element remains small, so that it is easily stiffened by flow.

In embodiments, some geometries allow of the stiffening element allow vaginal secretions to flow therethrough.

An aspect of some embodiments of the invention relates to a method of managing incontinence using an adjustable tension ring. Optionally, the management is self-management or by a caregiver.

Optionally, adjustable tension rings according to various embodiments of the invention may be useful in management of urinary incontinence, for example stress incontinence, and/or urge incontinence, for women who perform high impact physical activity and/or for elderly or otherwise partly or completely incapacitated patients.

Blows sustained in high impact physical activity can cause pressure surges in the bladder. In embodiments of the invention, a person in need thereof temporarily increases the urethral pressure until they reach a bathroom. Optionally, the adjustable tension ring is used for short periods of time, for example during a coughing fit.

Optionally, the increase is provided by a caretaker, for example at home care or in an old-age home. In an alternative embodiment, the tension is kept high until urination is desired.

In embodiments of the invention, scheduling of care-taking of patients is controlled using the device so that the caretaker can treat patients in a convenient order or allow for a delay in providing relief to a patient, if some cause for delay occurs.

The term "ring" as used in this application refers to a loop of any shape which can provide additional support to the urethra. For example, a ring according to some embodiments of the invention can be biased inward towards the central axis (creating a plus sign shaped support ring) or can consist of substantially straight segments (creating a quadrilateral, hexagonal or octagonal shaped or other polygonally shaped ring or be undulating or have a dimension perpendicular to the ring plane, for example a hollow cylinder or cone. Different shaped rings are optionally utilized depending on the needs of the individual wearer.

In an exemplary embodiment of the invention, the ring has an inner support, optionally in the form of extensions that extend out of or within the ring plane.

In an exemplary embodiment of the invention, the device is provided in a bag, which bag is also inserted into the vagina. Optionally, the bag serves to add additional support to the vagina. Alternatively, the device is designed to provide sufficient support without a surrounding bag.

Optionally, small notches are provided on the ring. In embodiments of the invention, the notches are sized to prevent entry of the urethra therein. Additionally or alternatively, the ring can be of constant diameter and/or wall thickness along its entire length, or different diameters and/or wall thickness along its length.

Optionally, variable diameter or wall thickness contributes to a desired pressure in an area of the ring aligned with the urethra. Optionally the ring may be held by another intra-vaginal device. Optionally the ring is perpendicular to the intra-vaginal device. Optionally the ring is located in front of the perpendicular device or at any portion of the perpendicular intra-vaginal device.

An aspect of some embodiments of the invention relates to an intra-vaginal device inflatable by means of a bead moved along a tube containing a flowable material, such as soft silicone or a fluid, such as saline or gas. In embodiments of the invention, moving the bead causes a small amount of fluid, for example, less than 5 cc, less than 1 cc, or less than 0.5 cc to move into the device. In embodiments of the invention, a complete operation of the device (e.g., stiffening or softening is) applied by a single motion of the bead. Optionally, the bead remains in place by friction thereof with the tube.

Optionally, the bead does not provide a complete seal and fluid slowly leaks past the bead. Alternatively or additionally, the bead is elastically primed to return to a previous position, for example, being mounted on an axially elastic sheath over the tube.

In embodiments of the invention, the tube is integral with the stiffening element. Alternatively or additionally, the tube is a loop.

In embodiments of the invention, the tensioning mechanism comprises a wire inserted in a lumen of the element and attached at one point thereto, such that when the wire is retracted (e.g., using a bead) the element compresses slightly and is tensioned thereby. Optionally, the wire is elastic and pulls the bead back, at a rate depending, at least in part, on friction between the bead and a tube surrounding the wire. In an alternative embodiment, the ring is tensioned when the wire is advanced into the element.

In embodiments of the invention, there is provided an apparatus for amelioration of incontinence in a female subject, the apparatus comprising a stiffenable element adapted for intra-vaginal insertion and a tensioning mechanism adapted for selectively increasing and decreasing a rigidity of the element after insertion thereof. Optionally, the element comprises a ring.

Optionally, the ring is sized for intra-vaginal insertion.

Optionally, the ring is adapted to switch from a first configuration outside the body to a second configuration after intra vaginal insertion.

Optionally, the switch from the first configuration to the second configuration is performed mechanically.

Optionally, the tensioning mechanism comprises a reservoir of fluid and a transfer element adapted to move at least a portion of the fluid into an inner lumen of the ring.

Optionally, the ring comprises an inner lumen in fluid communication with the tensioning mechanism.

Optionally, the tensioning mechanism comprises a static state and a second state which is biased to change back to said static state.

Optionally, the fluid comprises a liquid.

Optionally, the fluid comprises a gas.

Optionally, the reservoir of fluid comprises an additional length of tubing defining a lumen in fluid communication with the inner lumen of the tubing of the ring.

Optionally, the transfer element comprises a constricting element axially translatable along the reservoir.

Optionally, the apparatus includes at least one transverse support element engaging the ring.

Optionally, the apparatus includes an anchor extending axially away from the ring, the anchor adapted to reduce translational motion of the ring with respect to a vaginal wall.

Optionally, the apparatus includes at least one through aperture for flow of vaginal secretions therethrough.

Optionally, the apparatus is adapted to function in a substantially same manner irrespective of an orientation thereof around an axis of said vagina.

In embodiments of the invention, there is provided a method for ameliorating incontinence, the method comprising intra-vaginally inserting a non-space filling tensional element so that at least a portion of the element contacts an organ through a vaginal wall, and selectively increasing and decreasing a pressure applied by the element to the vaginal wall.

In embodiments of the invention, there is provided a method for relieving incontinence, the method comprising providing an intra-vaginal ring with at least a portion of the ring contacting an organ through a vaginal wall, and adjusting a pressure applied by the ring to the vaginal wall so that incontinence relief is provided.

In embodiments of the invention, there is provided a method of regulating a degree of incontinence control, the method comprising providing an intra-vaginal ring configured to apply a selected degree of pressure to an organ through a vaginal wall and varying the pressure responsive to a need for incontinence control.

The present invention relates, in some embodiments thereof, to the use of an intra-vaginal device for amelioration of female incontinence and methods for use thereof. Before explaining at least one embodiment of the invention in detail, it is to be understood that the invention is not necessarily limited in its application to the details of construction and the arrangement of the components and/or methods set forth in the following description. The invention is capable of other embodiments or of being practiced or carried out in various ways.

Exemplary Method of Incontinence Device Use

FIG. 1 is a simplified flow diagram of a method 100 for management of incontinence according to embodiments of the invention. Method 100 employs an adjustable tension ring inserted in the vagina to ameliorate symptoms of incontinence. Optionally, symptoms are relieved or reduced only when the ring is in place in the vagina. In embodiments as ring tension increases, pressure applied to the urethra through the vaginal wall increases.

In some embodiments, pressure is applied perpendicular to the urethral axis. In some embodiments of the invention, pressure is applied at a non-perpendicular angle. Optionally, the device comprises multiple interconnected rings, optionally having parallel planes, alternatively, having intersecting planes. This may assist in insertion, anchoring and/or ensuring continence. Optionally, the rings are of any design shown herein and optionally share a same tensioning mechanism (e.g., a same fluid source. In general, the pressure can serve to narrow a lumen of the urethra and/or obstruct a flow of urine therethrough. Optionally, pressure can be applied directly or by stretching vagina; this may depend on insertion method or on device structure, for some embodiments.

In embodiments of the invention, treatment is not of urethra, but of bladder neck (e.g., support or elevation) or is of the form of organ prolapse treatment. For such uses, an applicator for guiding deeper insertion may be provided and/or an anchor position and/or size may be different. Optionally, the device size is formed to be appropriate to the use. In some embodiments of the invention, patient size variations (for urinary continence) are provided for by allowing variable stiffness levels.

At 110 of depicted method 100, the ring is intra-vaginally inserted so that at least a portion of the ring contacts a portion of a urethra through the vaginal wall and/or bladder neck and/or stretches the vagina. In embodiments of the invention, the ring is sufficiently flaccid at this stage to be easily deformable. Optionally, ease of deformation contributes to ease of insertion. Optionally, the ring can be flaccidized depending on comfort and ease of insertion.

In some embodiments of the invention, the ring is placed in an applicator in a collapsed state and deployed therefrom into the vagina. Optionally, insertion into the vagina is performed without regard to ring orientation (360°). Optionally, the device is supplied to the user collapsed within an applicator. In embodiments of the invention, ring orientation does not significantly affect function because the ring works by stretching the vaginal wall.

At 120 of depicted method 100, the user increases a pressure applied by the ring to the vaginal wall. In embodiments of the invention, pressure applied by the ring to the vaginal wall is conducted to the urethra and reduces a tendency towards incontinence. Optionally, increasing 120 is performed when the patient (or caretaker) feels and/or anticipates a need.

In embodiments of the invention, the pressure increase (120) is achieved by introducing 130 fluid into a lumen of tubing forming the ring. The fluid can be a gas (e.g. air, $CO_2$ or nitrogen) or a liquid (e.g. water, saline or a buffer). Optionally, the fluid is colored with a dye so as to be visible to the user. One means of introducing 130 fluid into a lumen of tubing forming the ring is diagrammed at 140 and 150.

In embodiments of the invention, additional tubing is joined 140 to the tubing forming the ring so that a lumen of the additional tubing is in fluid communication with the lumen of the tubing forming the ring. The lumen of the additional tubing optionally serves as a fluid reservoir or conveys fluid from an external reservoir.

According to this embodiment, at 150 fluid is transferred from or via the additional tubing into the lumen of the tubing forming the ring. In this embodiment of the invention, transfer 150 serves as a means of introducing 130.

In embodiments of the invention, the pressure increase is used to ameliorate incontinence in physically or mentally handicapped with incomplete control of continence (e.g. after spinal injury, or cerebro-vascular accidents) that are not able to reach the toilet on time. Optionally, these women benefit from an incontinence control mechanism adapted to function for prolonged periods. In embodiments of the invention, a device with a variable tension ring allows for control of continence (via pressure increase 120) when needed and for micturation, either when feeling the urge to void or as a scheduled voiding after a certain period of time (by reducing pressure 180). In embodiments of the invention, a separate electrical actuator and/or remote is provided for moving fluid from the reservoir. Optionally, the actuator is designed to receive a device tubing as described herein and move transfer element 220 (describe below), to control tension. Alternatively, the actuator includes the transfer element. This remote/actuator may be multi-use (e.g., including mechanical force transducers or a battery and a motor or linear actuator) and the tubing and device be disposed of after a few hours or days.

Optionally, the device is adapted to be left in place for many hours to one or more days. During this period, tension in the ring may optionally be increased for minutes (e.g. during a coughing fit) to hours (e.g. during a bus ride).

Optionally, if high tension in the ring is left for too long (e.g. if a patient or caregiver forgets to release the tension) fluid can leak out of the ring. In embodiments of the invention, occasional incontinence is acceptable as a safety measure to prevent bladder damage. Optionally, the leakage time is set, for example, being three hours. Optionally or alternatively, a time is coupled to the device and/or work by a caregiver and/or patient to give warning before the incontinence device deactivates.

In another embodiment of the invention, the pressure increase is used to ameliorate incontinence in women with a combination of stress urinary incontinence and urge incontinence (termed mixed incontinence). Optionally, use of a variable tension ring allows mixed incontinence patients to reach a toilet without wetting themselves, and urinate when the pressure within the ring is reduced 180. Optionally, use of a variable tension ring allows patients with urge incontinence to overcome brief urges. In embodiments of the invention, a device for mixed incontinence patients has two settings—one for all day and one for relatively short periods of "urge". Optionally, the reservoir is marked. Optionally, the markings divide a continuous scale into discrete units. Optionally, markings at intervals of 1 to 5 mm are appropriate. Optionally, the markings are enhanced or replaced by slight indentations or bumps and/or changes in frictional behavior of the tube vis-à-vis the transfer element. In some cases, a large response in rigidity of ring 202 from a small incremental movement of transfer element 220 with respect to reservoir 210 is desired. In other embodiments, a small response in rigidity of ring 202 from a large incremental movement of transfer element 220 with respect to reservoir 210 is desired.

In yet another embodiment of the invention, a user inserts 110 the intra-vaginal ring and increases 120 pressure applied by the ring to the vaginal wall prior to an anticipated stress event. Optionally, the stress event comprises physical contact (e.g. a sporting event or game) and/or a period during which toilet facilities will not be readily available (e.g. travel in a bus, car or airplane). The term "sporting event" as used herein includes, but is not limited to, bicycle riding, horseback riding, running, other track and field events, skating (roller or ice), skiing, parachuting, swimming, diving and bungee jumping. The term "game" as used herein includes, but is not limited to, soccer, hockey (field or ice), rugby, boxing, wrestling, judo, karate, handball, racquetball, tennis, basketball, volleyball and other competitive games in which rough physical contact is likely and/or possible.

In embodiments of the invention, the device is employed to prevent incontinence associated with coughing and/or sneezing spells or at times when a diaper is off.

After use (e.g. once a period of anticipated stress is concluded; for example after a soccer game), the user removes 190 the ring. In embodiments of the invention, removal 190 is preceded by reducing 180 pressure applied by the ring to the vaginal wall. One way to reduce 180 pressure is to remove 132 fluid from a lumen of the ring. Optionally, removing 132 fluid renders the ring flaccid and/or flexible. In embodiments of the invention, flaccidity and/or flexibility contribute to an ease of removal 190.

In embodiments of the invention, a string is attached to the device. Optionally, pulling on the string contributes to an ease of removal 190. Alternatively or additionally, the tubing also serves as a string and is optionally made flaccid enough (e.g., when full and/or empty) to be as unobtrusive as possible.

In embodiments of the invention, supporting 160 of the ring during use is performed. Supporting 160 can be, for example, by means of at least one transverse support element as described hereinbelow. Optionally, the ring has a shape set by the elements and inflation makes the shape rigid so that a tendency to deform in response to vaginal wall pressure is decreased.

In embodiments of the invention, the ring is anchored to resist axial and/or radial translation within the vagina. Anchoring 170 can be, for example, by means of an anchor as described hereinbelow.

In embodiments of the invention, the inserted device has a high pressure phase (see 120) and a low pressure phase (see 180). Optionally, the high pressure phase initiated at 120 is temporary, and pressure to the urethral lumen is relieved at 180. In those embodiments of the invention where the device is used over a long period of time, a repeated fluctuation between high and low pressures within the ring is optionally institute. Optionally, the user should reduce pressure (180) within the ring either in response to feeling of the urge to urinate or at constant intervals (e.g. every 90-120 minutes), empty the bladder, and elevate the pressure (180) within the ring again.

In embodiments of the invention, pressure increase 120 and/or reducing pressure 180 can be conducted incrementally. Optionally, the user can select any pressure above a minimum pressure applied by ring 202 when its lumen is empty of fluid and a maximum pressure achieved when a maximum amount of fluid is present in the lumen of ring 202.

Incontinence Ameliorating Devices

Figures 2A, 2B:
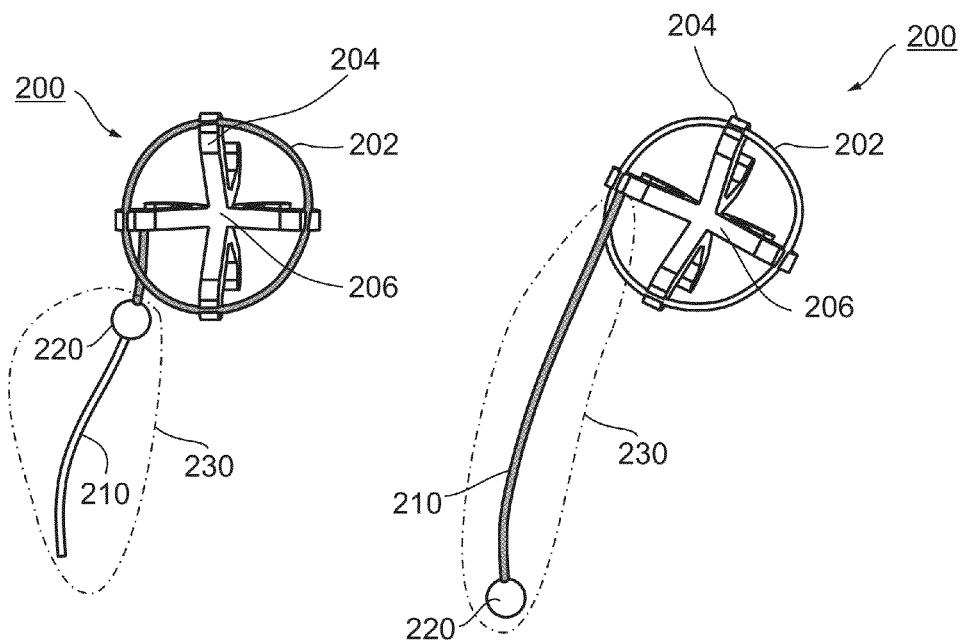
FIGS. 2a and 2b are top views of an adjustable tension incontinence device embodiment in rigid and soft states respectively, according to some embodiments of the invention.

FIGS. 2a and 2b are top views of an intra-vaginally deployable incontinence amelioration apparatus 200 in its non-operative and operative state respectively. In the depicted embodiment, functionality of apparatus 200 is related to a degree of rigidity in an adjustable tension ring 202.

Embodiments of the invention are constructed so that the device allows for free passage of vaginal and/or cervical secretions out of the body through the ring.

In FIG. 2a an inner lumen of tubing forming ring 202 is substantially empty so that the ring is soft. A soft ring 202 is suitable for insertion and/or placement and/or alignment and/or removal. Soft materials suitable for ring construction are described below.

In FIG. 2b an inner lumen of tubing forming ring 202 is filled with a fluid so that the ring is more-rigid. In embodiments of the invention, the vagina applies pressure to rigid ring 202 and the pressure is transferred to the urethra through the vaginal wall. In embodiments of the invention, a degree of rigidity contributes to an amount of the pressure exerted on the urethra and/or varies with an amount of fluid introduced into the lumen.

In embodiments of the invention, ring 202 is sized for intra-vaginal insertion. Optionally, sizing for intravaginal insertion comprises a ring diameter of 25 to 65 mm. In embodiments of the invention, smaller women or young girls are fitted smaller rings. Optionally, larger (vaginal size) women are fitted with larger rings. In embodiments of the invention, an outer diameter of the tube is 2, 3, 4, 5, or 6 mm or lesser or intermediate or greater diameters. Optionally, a larger outer diameter distributes applied pressure across a grater area of the vaginal wall. Optionally, the contact surface of the tube with the wall is shaped for comfort, for example by being flattened (e.g. on a side which will contact the vaginal wall) and/or by having rounded edges and/or by being fitted with a soft comfort layer on a side which will contact the vaginal wall.

Depicted apparatus 200 includes a tensioning mechanism 230 adapted for increasing a rigidity of the tubing. In the depicted embodiment, tensioning mechanism 230 comprises a reservoir 210 of fluid and a transfer element 220 adapted to move at least a portion of the fluid from the reservoir into an inner lumen of tubing forming ring 202. According to various embodiments of the invention, the fluid can comprise a liquid and/or a gas. Optionally, reservoir 210 and ring 202 are formed from a single length of tubing.

In embodiments of the invention, reservoir 210 is sized and shaped so that a sufficient amount of fluid to cause a desired tension in ring 202 is transferred by a single motion of transfer element 220. Optionally, reservoir 210 is characterized by a greater inner volume per unit length than ring 202. Alternatively, it has a same or greater such volume. Optionally, the reservoir has a larger volume due to its length.

In embodiments of the invention, the tubing has an internal volume of less than 200%, 100%, 50%, 30%, 20% or intermediate percentages of the volume of the ring itself.

In embodiments of the invention, when the ring is nearly full (for example 99% full) of fluid adding a last small amount (for example 1%) makes a great contribution to rigidity. Optionally, a volume of fluid provided in the tube can be small relative to a total lumen volume of the ring.

In embodiments of the invention, as a ratio of inner volume per unit length between reservoir 210 and ring 202 increases, an amount of motion of transfer element 220 needed to transfer a sufficient amount of fluid to cause a desired tension in ring 202 decreases.

In the depicted embodiment of the invention, reservoir 210 comprises an additional length of tubing defining a lumen in fluid communication with the inner lumen of the tubing of ring 202. According to this embodiment of the invention, axial translation of transfer element 220 along the tubing of reservoir 210 towards ring 202 moves at least a portion of the fluid from the reservoir into an inner lumen of tubing forming ring 202. In the depicted embodiment, transfer element 220 comprises a constricting element (e.g. a bead or ring) with an inner diameter sufficiently small to collapse the lumen of the tubing of reservoir 210 as transfer element 220 advances. Translation of a collapsed point of the lumen of reservoir 210 towards ring 202 reduces a volume of fluid in reservoir 210 by urging the fluid forward into the lumen of tubing forming ring 202. In FIGS. 2a and 2b, the fluid is provided as a colored liquid. In FIG. 2b, transfer element 220 has been advanced along the tubing of reservoir 210 all the way to ring 202. Substantially all of the colored fluid is visible in ring 202 at this stage while reservoir 210 is substantially empty. In embodiments of the invention, a relative volume of reservoir 210 and the lumen of tubing forming ring 202 contributes to a degree of tension and/or rigidity imparted to ring 202 by advancing tensioning mechanism 220.

In embodiments of the invention, after insertion 110 (FIG. 1), at least a portion of tube 210 and/or transfer element 220 remain outside the vagina. Optionally, an extra-vaginal position contributes to ease of manipulation (e.g., for increasing pressure 120 and/or reducing pressure 180)

FIGS. 2a and 2b also depict a pair of transverse support elements 204 engaging ring 202. Optionally, transverse support elements 204 are joined by a hub 206.

In some embodiments, the ring is used in a normally-rigid mode, in which it remains rigid until fluid is pulled out. Optionally, the transfer element is designed to return to its original position, for example, being mounted on an axially elastic sheath. Alternatively or additionally, the transfer element does not provide a complete seal and some leaking occurs, optionally timed to match a safety period (e.g., of several minutes or hours), when the pressure within the bladder rises and overcomes the intra-urethral pressure.

Figure 3:
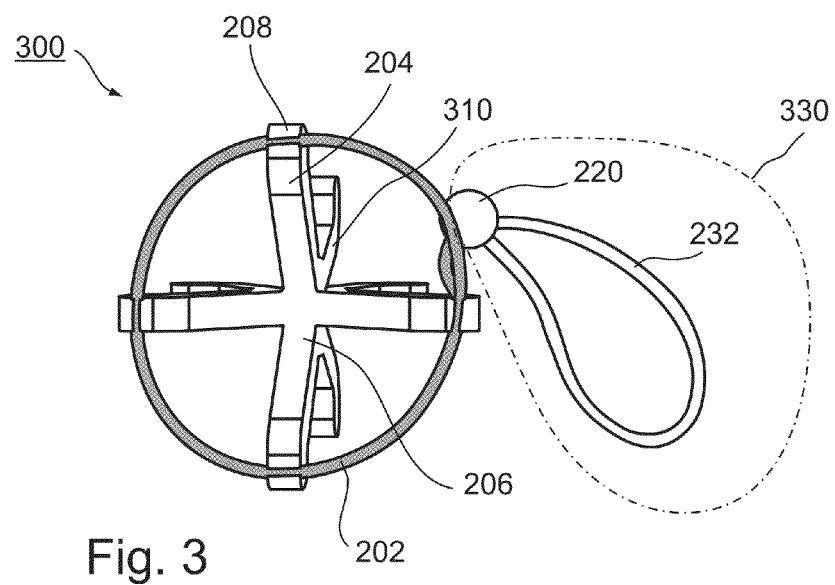
FIG. 3 is a top view of an adjustable tension incontinence device embodiment in a rigid state illustrating an additional tension adjustment mechanism, according to some embodiments of the invention.

FIG. 3 is a top view of an intra-vaginally deployable incontinence amelioration apparatus 300 in its operative state. The depicted apparatus 300 is similar to apparatus 200 except that tensioning mechanism 330 comprises a reservoir 232 of fluid configured as a loop. Transfer element 220 encircles two thicknesses of tubing comprising reservoir 232. In the depicted embodiment, each increment of axial translation of transfer element 220 along the loop of reservoir 232 transfers twice as much fluid as a similar increment applied to the straight reservoir 210 of apparatus 200. Optionally, use of a loop reduces a need for sealing.

In FIG. 3, anchor arms 310 extending axially away from ring 202 is visible. In embodiments of the invention, anchor arms 310 are inserted into the vagina and ring 202 follows it. Optionally, anchor arms 310 functions to limit axial translation of ring 202 within the vagina.

Anchor arms 310 can optionally be of a type described in WO 2005/087154 and/or WO 2005/087153 and/or WO 2004/103213 and/or U.S. Provisional Application 60/762,059 filed Mar. 17, 2005 and/or U.S. Provisional Application 61/006, 927 filed 6 Feb. 2008. The disclosure of each of these applications is fully incorporated herein by reference. Optionally, the ring is mounted on an incontinence device as described therein and serves to stiffen the device selectively to provide better prevention and/or control of incontinence.

Optionally, anchor arms 310 can be characterized by any configuration adapted to hold ring 202 in place for a relevant period of time. Relevant periods of time can vary from hours to days to weeks.

Also visible in FIG. 3 are engagement grooves 208 in transverse support elements 204. In embodiments of the invention, grooves 208 engage and retain ring 202 at or near distal ends of elements 204.

In embodiments of the invention, a degree of friction between transfer element 220 and tubing of reservoir 210 or 232 is sufficient so that pressure of fluid in ring 202 does not push transfer element 220 away from ring 202 along the reservoir.

Optionally, transfer element 220 is provided with a release button so that axial translation of element 220 away from ring 202 can be easily initiated by a user to release fluid from ring 202.

Optionally, the user manually overcomes friction between transfer element 220 and tubing of reservoir 210 or 232 in order to move element 220 away from ring 202 to release fluid from ring 202.

In FIG. 3, transfer element 220 is activated so that ring 202 is filled with fluid and reservoir 232 is empty of fluids.

Figure 4:
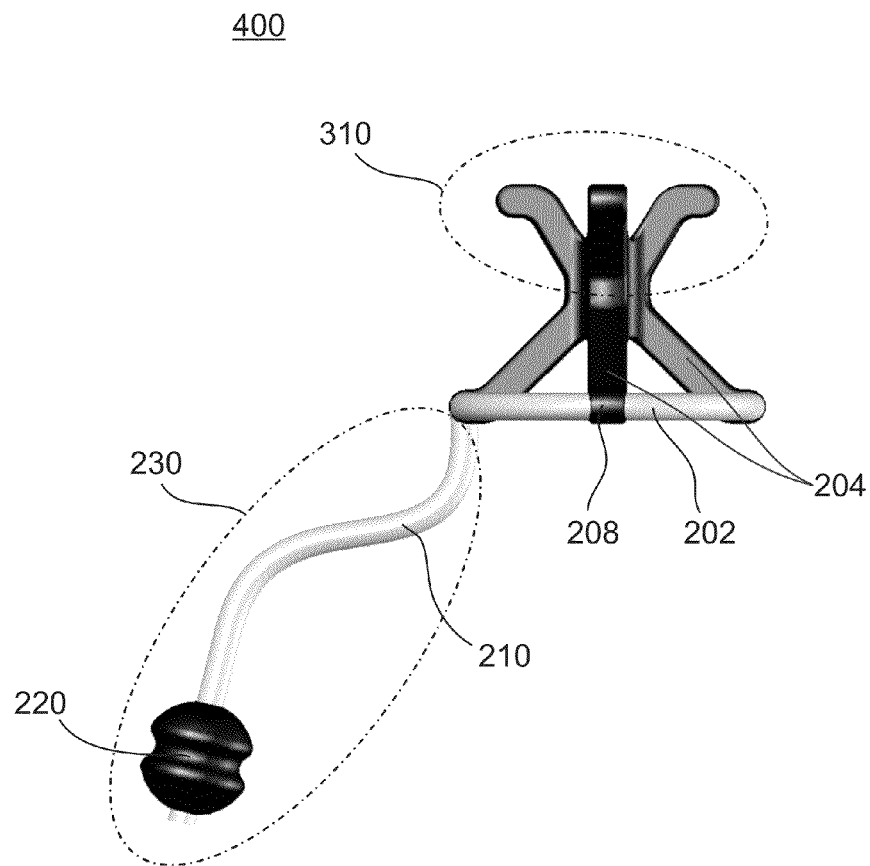
FIG. 4 is a side view of an incontinence device embodiment having an adjustable tension ring in a soft state, according to some embodiments of the invention.

FIG. 4 is a side view of an additional device 400, in which engagement of ring 202 is via sleeves 208. In embodiments of the invention, reservoir 210 is connected to ring 202 in a "T" connection so that fluid entering ring 202 from reservoir 210 can flow in either direction around the ring. Optionally, the "T" connection is formed by engagement grooves 208 (not visible in this view) which engage ends of ring 202 and reservoir 210 and provide a channel of fluid communication between them.

In embodiments of the invention, distal ends of transverse support elements 204 are resilient with respect to pressure applied by a vaginal wall. Optionally, increasing rigidity of ring 202 contributes to an increase in resilience of transverse support elements 204.

In another embodiment of the invention, distal ends of transverse support elements 204 are not resilient with respect to pressure applied by a vaginal wall. Optionally, increasing rigidity of ring 202 is a primary, optionally sole, source of resilience of transverse support elements 204. Optionally, varying an amount of fluid in ring 202 provided varying degrees of resilience.

In embodiments of the invention, three resilience states are provided: (1) no applied resilience and no incontinence control; (2) medium resilience which controls incontinence but permits desired micturation and (3) high resilience which is sufficient to prevent micturation or involuntary leakage.

Figure 5:
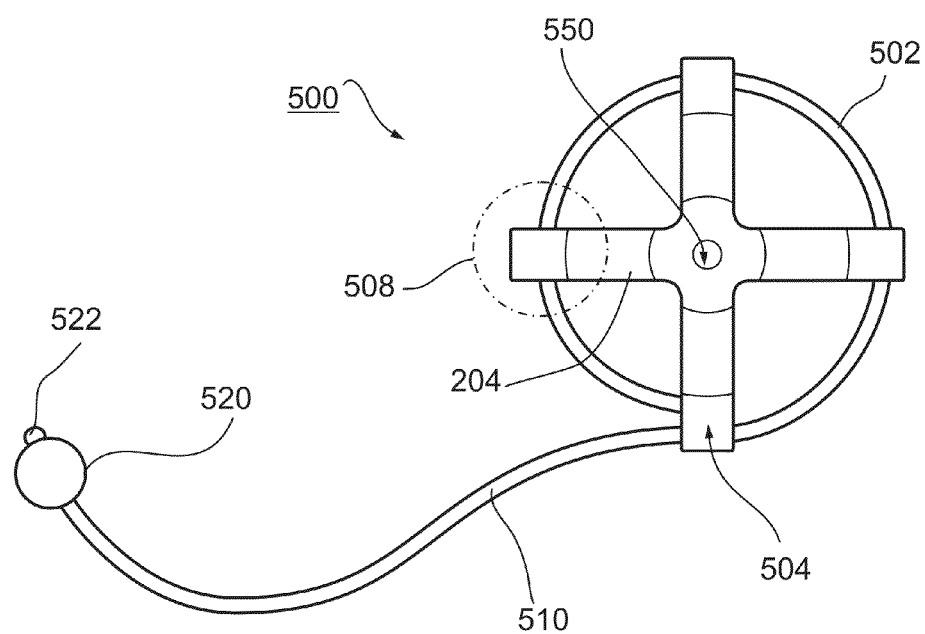
FIG. 5 is a top view of another adjustable tension incontinence device embodiment, according to some embodiments of the invention.
Figures 6A, 6B:
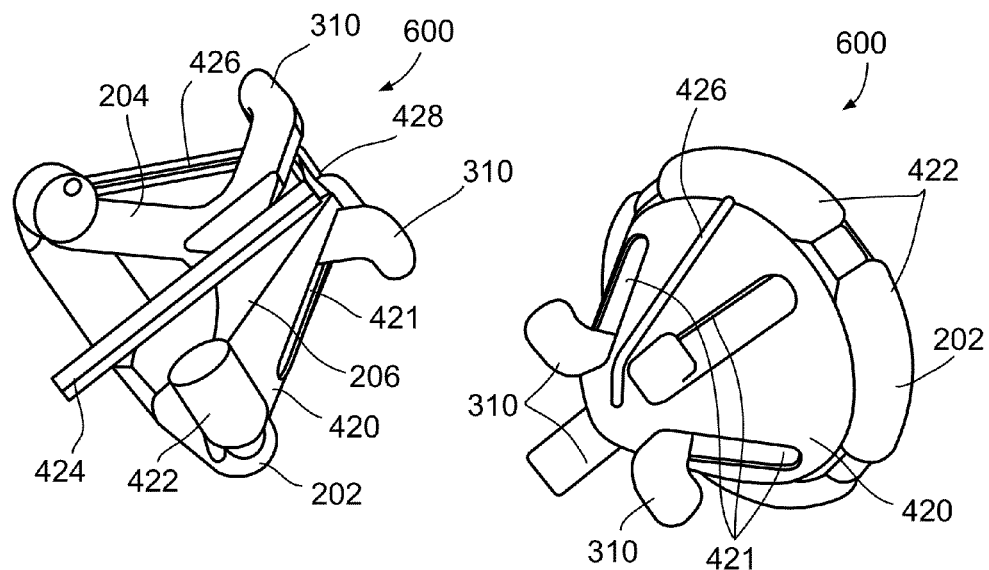
FIGS. 6A-6D show a cone shaped adjustable incontinence device, according to an exemplary embodiment of the invention.
Figures 6C, 6D:
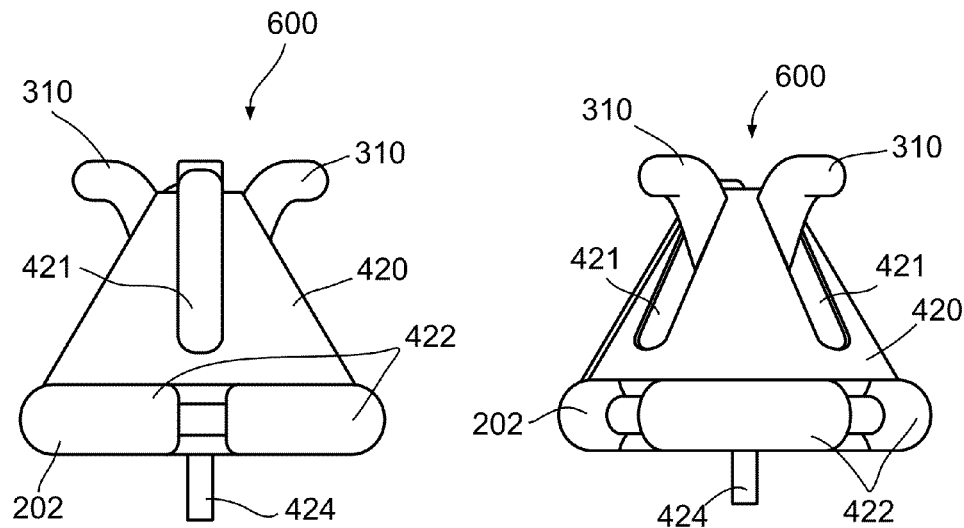

FIG. 5 is a top view of another adjustable tension ring 500 according to an additional embodiment of the invention. In the depicted embodiment, sleeves 508 of transverse support elements 204 engage a single continuous piece of tubing which comprises ring 502 and reservoir 510. In the depicted embodiment, transfer element 520 is constrained from moving off of reservoir 510 by sealed end 522. Optionally, sealed end 522 serves to retain fluid in reservoir 510 in addition to, or instead of, constriction by transfer element 520. Depicted adjustable tension ring 500 is different from other embodiments described hereinabove in that distal end 504 (optionally sealed) is engaged by transverse support element 204 but is not directly attached to reservoir 510. End 504 and reservoir 510 are depicted as being at different radial distances from s center hub 550 of ring 502. Optionally, end 504 and reservoir 510 are position one above the other so that a radius of ring 502 is more uniform (not pictured). In embodiments of the invention, hub 550 is attachable to anchor arms 310 (FIGS. 3 and 4). Optionally, hub 550 permits rotation of ring 502 with respect to the anchor. Optionally, embodiments of the type depicted in FIG. 5 are more economical to produce and/or assemble than those of FIGS. 2, 3 and 4.

Alternative Device Design

As seen in FIGS. 6A-6D, an alternative incontinence ameliorating device 600 includes a hub 206 located between support arms 204 and anchor arms 310. Optionally, the use of a hub allows the ring to be segmented and/or supports more uniform flow of fluid into the ring. Device 600 also illustrates the use of a cone-like covering (e.g., skirt) for a part of the device. This feature may be used with or instead of the hub and may be useful, for example, for stabilization and/or for supporting fluid passageways.

An optional skirt 420 surrounds device 600 so that anchor arms 310 protrude through openings 421 in skirt 420. Skirt 420 has a conus shape and may be made of various materials such as nylon polyurethane, non woven cloth, and/or silicone. Optionally, openings 421 are selected (e.g., size and/or shape) to support flow of vaginal secretions therethrough.

In embodiments, a ring 202 comprises fluid chambers 422. Fluid chambers 422 may be separate, an optionally utilizing separate fluid tubes 426 to fill each fluid chamber 422, or may be interconnected by a tube so that one fluid tube 426 supplies fluid to all fluid chambers 422 (e.g., via a fluid hub 428). The number of such fluid chambers 422 may be between one and eight, for example four. Additionally, the cross sectional diameter of fluid chambers 422 may be, for example, between about 1, 2 or 4 and 10 millimeters.

A central fluid supply tube 424 passes axially through hub 206 and connects to fluid tubes 426, which in turn connect to fluid chambers 422.

Inner Stiffening Element

In an alternative set of embodiments, stiffening of the ring is provided by pushing by indirectly manipulating the ring, for example, using an internal element. Optionally, the internal element pushes out the ring, for example, using a plurality of arms. Optionally, the resilience of the arms helps determine the elastic response of the ring, which may be more comfortable than the direct pressure applied by an internally stiffened ring. Optionally or alternatively, direct stiffening of the ring may be more difficult to control with respect to comfort, while the use of stiffening arms may also a desired range of forces to be enforced and/or better control over intermediate stiffness provided.

FIGS. 7A-7D show an alternative incontinence ameliorating embodiment 700 having six support arms 204 (e.g., between 3 and 8, for example, 4), projecting from hub 206 that includes an internal volume 423 in which an inflatable element (e.g., balloon, compliant or non-compliant) 430 is situated. Balloon 430 gets its fluid supply from a fluid reservoir 450 that is squeezed to cause fluid to pass through a tube 432 into balloon 430. A valve for release of fluid 452 is optionally situated along tube 432.

Balloon 430 may attain various shapes in the inflated configuration, for example as a ball, as pictured, trapezoid, rhomboid or an ovoid shape.

Prior to insertion in the vagina, balloon 430 is in an uninflated configuration. Upon proper positioning of incontinence device 700 within the vagina, balloon 430 is inflated to cause support arms 204 to extend radially outward with a greater force so that ring 202 is fully stretched. With balloon inflated, ring 202 creates tension against the urethra. Optionally, the arms are predisposed to collapse radially inwards. Optionally or alternatively, deflating the balloon pulse the arm inwards.

In this and other embodiments, a plurality of stiffness settings are optionally provided, for example, 2, 3, 4, 6, 10 or more stiffness settings, optionally substantially continuous stiffness settings is provided. Optionally, the provision of multiple stiffness settings allows comfort to be better controlled.

In an exemplary embodiment of the invention, in this and other designs, the device is formed so as not to include moving parts that can pinch vaginal tissue between them, for example, by enclosing moving parts, by not having sharp angles and/or using skits that prevent tissue ingress into tight places.

Ring Pulling Embodiment

In some embodiments of the invention, the ring is stiffened by pulling it against a resistance, which causes distortion and/or radial extension of the ring. Optionally, the pulling force is applied form an anchor section of the device.

Figure 8A:
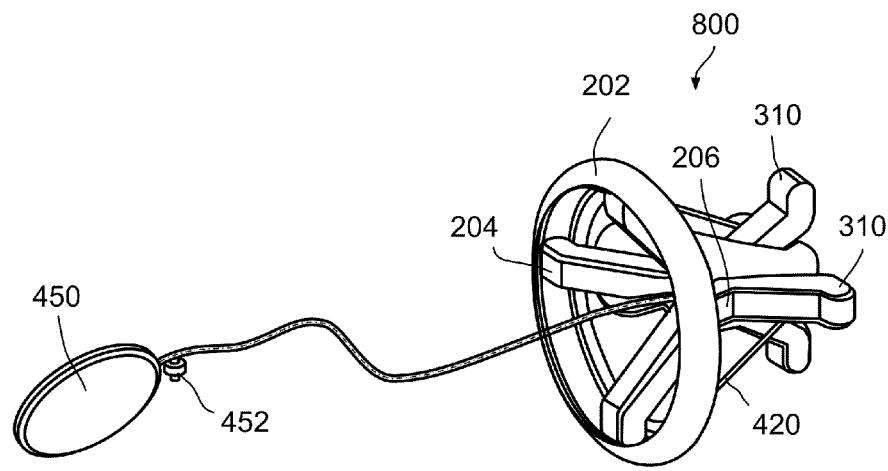
FIGS. 8A-8C show an adjustable incontinence device, having an inner inflatable section, according to an alternative exemplary embodiment of the invention.
Figure 8B:
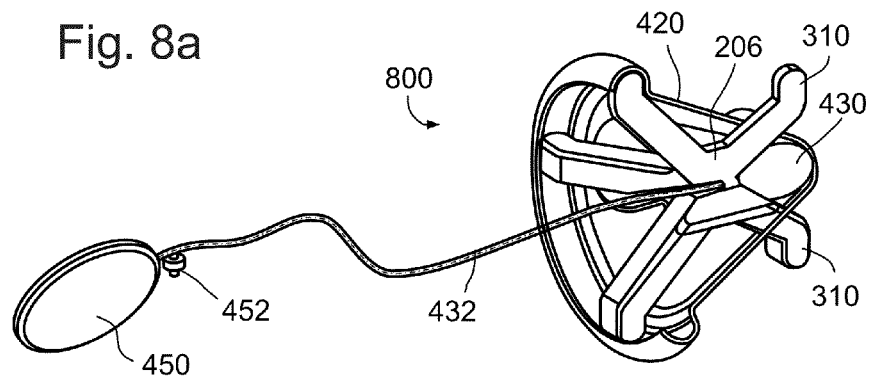
Figure 8C:
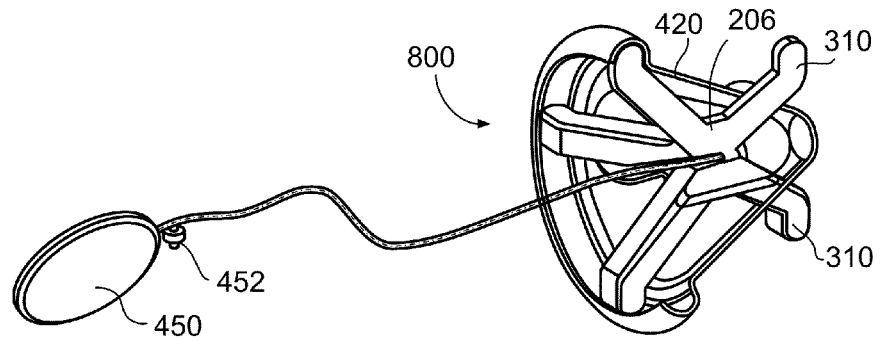

FIGS. 8A-8C show an alternative incontinence ameliorating embodiment 800 with skirt 420 made of a flexible material, and inflation balloon 430 located between skirt 420 and anchor arms 310. Optionally, the stiffness and/or elastic response of ring 202 is determined, at least in part, by an elasticity of skirt 420 (or other tension elements used) and/or resilience of arms 204.

As fluid is pumped into balloon 430, skirt 420 stretches and pulls ring 202 toward anchor 310 while causing support arms 204 to expand radially outwardly, radially expanding ring 202.

It should be noted that various of the mechanisms described herein may be selected between in order to achieve desired "give" and various functions of elastic resistance to certain movement sizes. Optionally or alternatively, the type of mechanism used may determine the coupling between distortion of different parts of the ring.

Non-Fluid Ring Pulling Embodiment

While many of the embodiments show using a fluid mechanism to achieve selectable stiffening, in an exemplary embodiment of the invention, other means are used, for example wire means.

Figure 9A:
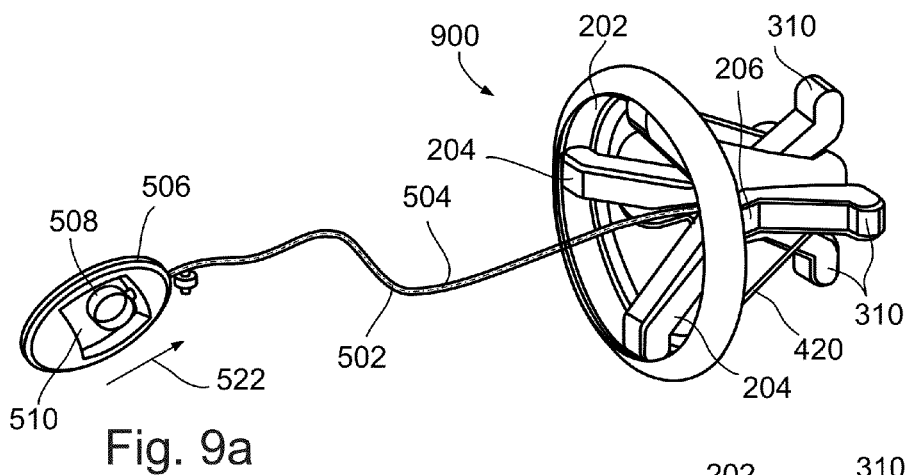
FIGS. 9A-9C show an adjustable incontinence device, having an inner tensionable section, according to an exemplary embodiment of the invention.
Figure 9B:
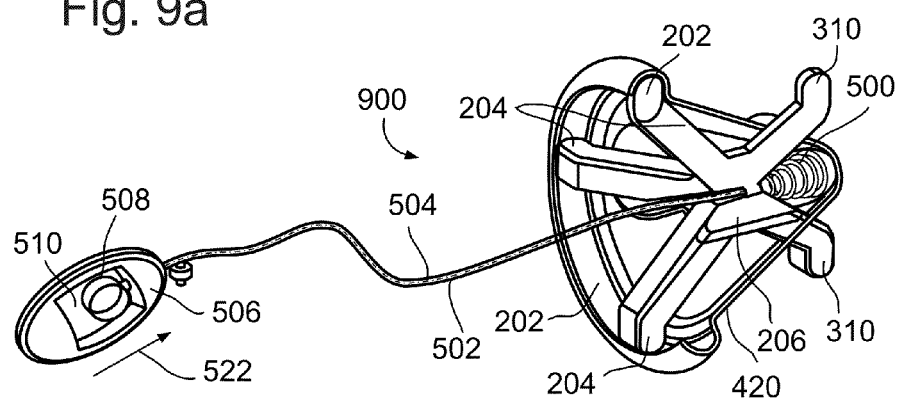
Figure 9C:
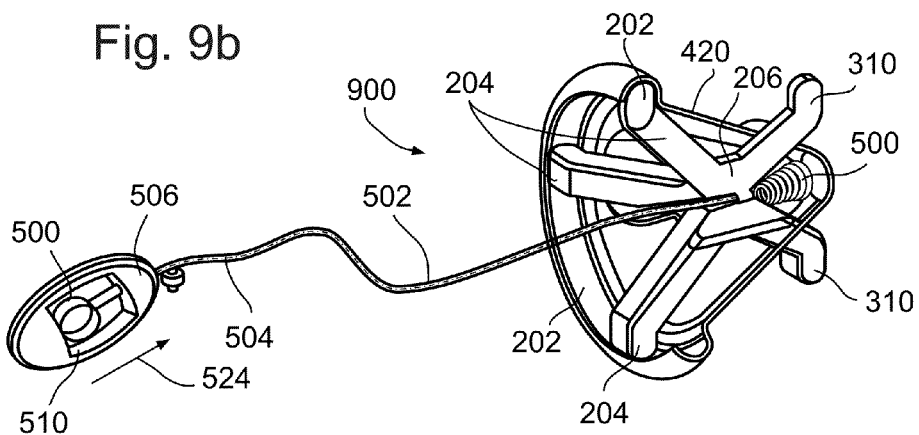

FIGS. 9A-9C show a spring incontinence ameliorating embodiment 900 having a spring 500 located between anchoring arms 310 and skirt 420.

Within a tube 502 and spring 500 is a wire 504 having a control ring 508 within a chamber 510 within a handpiece 506.

When control ring 508 is pressed in a forward direction 522, seen in FIGS. 9A and 9B, spring 500 expands, to cause skirt 420 to stretch and radially outwardly expand ring 202 and support arms 204. When control ring 508 is pulled in a rearward direction 524, as seen in FIG. 9C, spring 500 is collapsed, releasing tension on skirt 420 and support arms 204, thereby allowing collapse of support arms 204. Spring incontinence ameliorating embodiment 900 can thereafter be removed from the vagina. The spring may be, for example, has a resting position of closed or of open condition. Optionally, ring 508 can be locked in place and/or has sufficient friction to stay in place or to only move (on its own) at a slow, desired rate (e.g., several seconds or minutes to change state of the device).

In an exemplary embodiment of the invention, in this and/or other embodiments, the stiffening means is selected so that changing stiffness within a range of stiffness settings will not cause and/or allow axial movement of the device. Alternatively, a user may push in or pull out the device a small amount, as needed, optionally with the stiffening control serving as a pull wire.

Alternative Anchor Design

As noted above, the anchor section of the device may have different forms and/or functions. Various examples are described below.

Figure 10A:
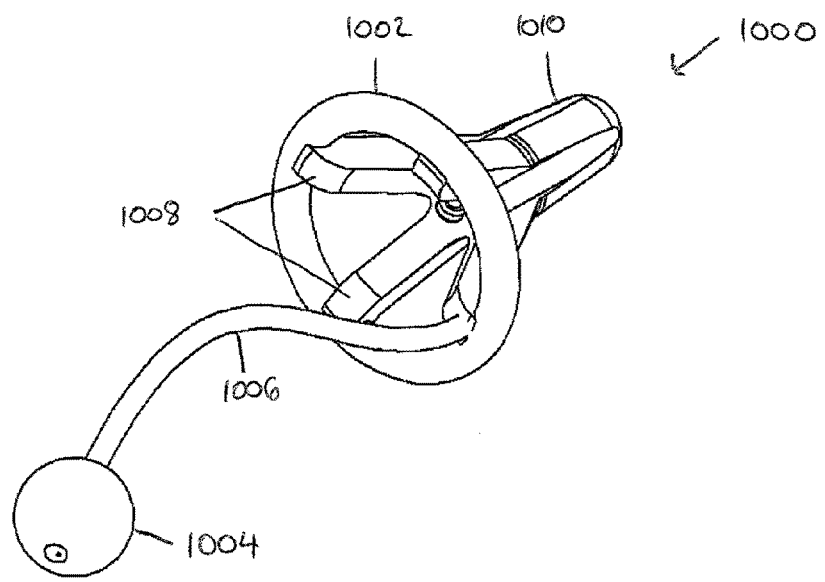
FIGS. 10A-10B show an adjustable incontinence device, with a first anchoring/stabilizing section design, according to an exemplary embodiment of the invention.
Figure 10B:
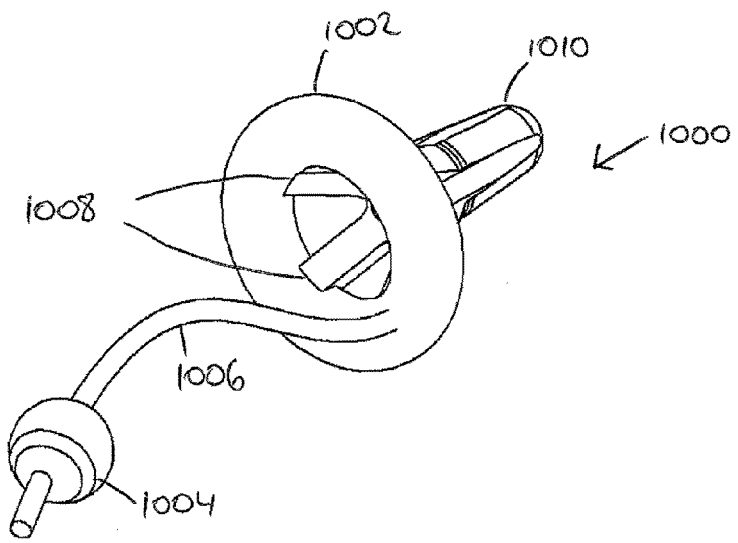

FIGS. 10A-10B show an adjustable incontinence device 1000, with a first anchoring/stabilizing section design, according to an exemplary embodiment of the invention. FIG. 10A shows the device in an unexpanded state and FIG. 10B shows the device in an expanded state.

Device 1000 has an inflatable tension ring 1002, which is inflatable using a tube 1006 and a bead 1004 (as described above, although other mechanisms may be used). As shown, ring 1002 is supported by a plurality of angulated arms 1008 which meat at an anchor extension 1010. Optionally, the extension is long enough to stabilize the device, for example, being 2, 3, 4, 5 cm long or intermediate lengths. Optionally, the extension is sized to prevent over insertion of the device.

Wire Based Tensioning and Prolapse Anchor

FIGS. 11A-11H show an adjustable incontinence device 1100, with a second anchoring/stabilizing section design, optionally suitable for prolapse treatment and an alternative tensioning element design, either of which features may be provided, according to an exemplary embodiment of the invention.

Figures 11A, 11B:
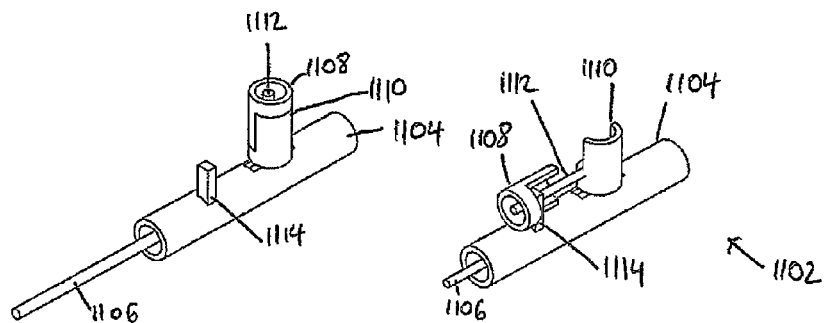
FIGS. 11A-11H show an adjustable incontinence device, with a second anchoring/stabilizing section design and an alternative tensioning element design, according to an exemplary embodiment of the invention.

FIGS. 11A and 11B show a tensionable element 1102, which shape changes when a wire 1106 is tightened therein. In FIG. 11A, a wire 1106 lies in a body 1104 and an extension 1110 extends away form body 1104. A position changing element 1108 is shown locked and/or supported by an optional projection 1114. When wire 1106 is pulled, this can tension a wire 1108 (which may be the same as wire 1106 or coupled thereto), so that element 1108 changes position, to the configuration shown in FIG. 11B.

Figures 11C, 11D:
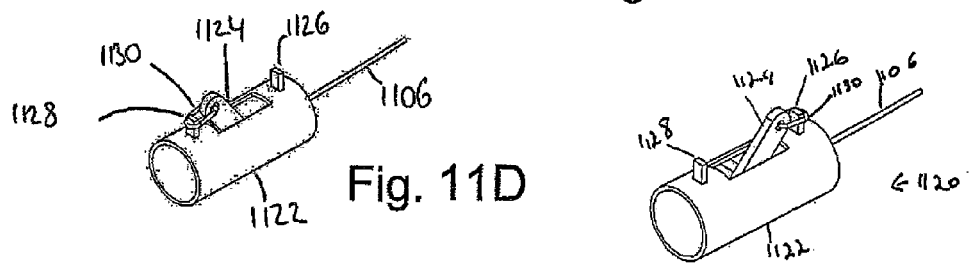

FIGS. 11C and 11D show a tensioning control 1120, in two wore positions (FIG. 11C is tensioned and FIG. 11D is untensioned, depending on the configuration and relative location of the pivot point of lever 1124). Wire 1106 lies in a body 1122 and a lever 1124 (or other control, such as a knob) couples the wire to the body. In the position of FIG. 11C, lever 1124 is oriented towards a distal side of the device and optionally coupled using a optional ring 1130 or other latch element to a post 1126. In the position of FIG. 11D, lever 1124 is oriented towards a post 1128 and optionally coupled thereto.

Figures 11E, 11F:
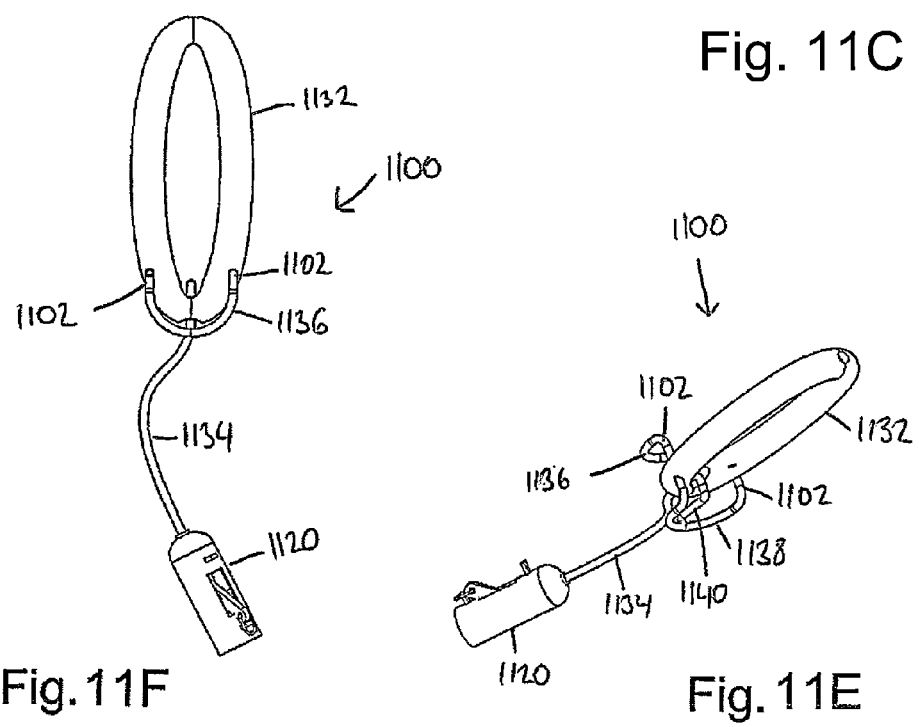
Figure 11H:
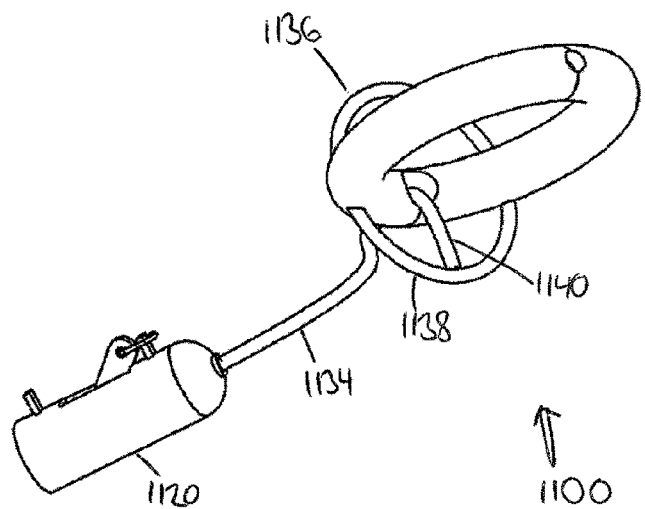
Figure 11G:
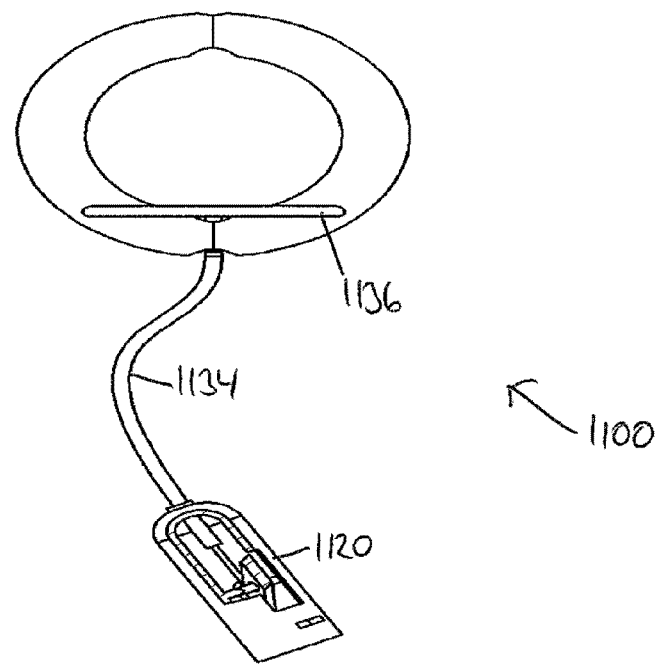

FIGS. 11E and 11F show device 1100 in an untensioned configuration, showing parts 1136, 1138 of an incontinence ring, a guide channel 1134 which may enclose wire 1106 and a wire conveying element 1140. Also shown is an exemplary usage of elements 1102. FIGS. 11F and 11G show the device in deployed form.

Also shown in FIGS. 11E and 11F is an anchor 1132 in the form of a ring. Optionally, the ring is stiff enough to be used for prolapse control. Optionally or alternatively, the ring is used for tensioning vaginal walls and assisting in some types of incontinence control.

Either or both of rings 1132 and the ring formed by elements 1136 and 1138 may use any of the tensioning mechanisms described herein or in U.S. provisional application Ser. No. 61/071,344 filed Apr. 23, 2008, inter alia, by inventor Elan Ziv. That application shows various ring tensioning elements, such as arms that extend apart and hold a ring open.

Optionally or alternatively, the two rings share a same extension mechanism with a single control.

Optionally or alternatively, in this and other embodiments, multiple incontinence and/or prolapse rings may be provided, for example, in parallel planes or at angles to each other.

In an alternative implementation, device 1100 serves for prolapse and the stiffenable ring formed by 1138 and 1136 is used for anchoring and/or stabilization. Optionally, incontinence control is provided by further stiffening.

In an exemplary embodiment of the invention, ring sections 1136 and 1138 are stiffened by the wire. Alternatively, the wire only unfolds the rings.

In this and other embodiments, dual prolapse and incontinence functions may be provided by suitable placement of the device (e.g., with the ring used for bladder neck support/elevation, and/or by providing a length sufficient so that the ring can provide mid-urethral support and a prolapse treating section is simultaneously positioned where it will provide prolapse support. Other prolapse support anchors may be provided as well, for example, in the form of an inflatable balloon or a ring attached to ring 1136, 1138 by a rod or flexible thread.

Fluid Based Tensioning and Prolapse Anchor

FIGS. 12A-12D show an adjustable incontinence device 1200 similar to the design of device 1100, in which a fluid mechanism (tube 1206, bead/pump 1208) is used to stiffen and/or unfold a ring 1204, instead of or in addition to a wire based mechanism. A ring 1202 for prolapse and/or anchoring may be provided as well. FIG. 12A shows the device in collapsed configuration and FIGS. 12B-12D is tensioned configuration. In an exemplary embodiment of the invention, when tension is somewhat reduced, the ring 1204 will only unfold partly and not to the configuration shown in FIG. 12A.

Basic Anchor

Figure 13A:
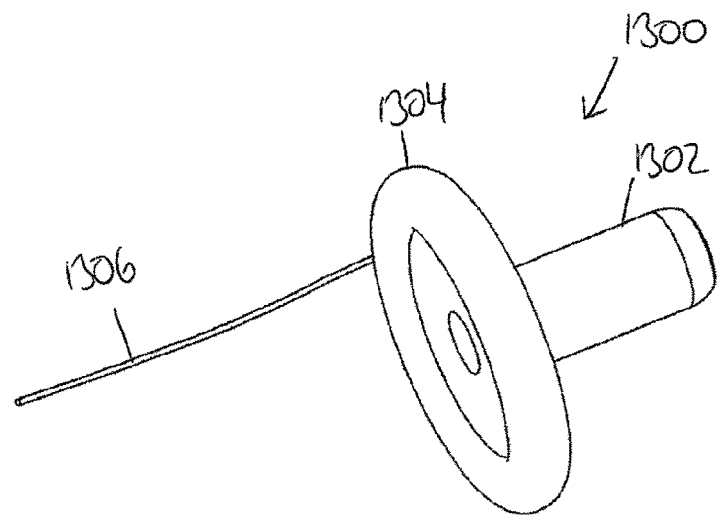
FIGS. 13A-13C show an adjustable incontinence device, with a third anchoring/stabilizing section design, according to an exemplary embodiment of the invention.
Figure 13B:
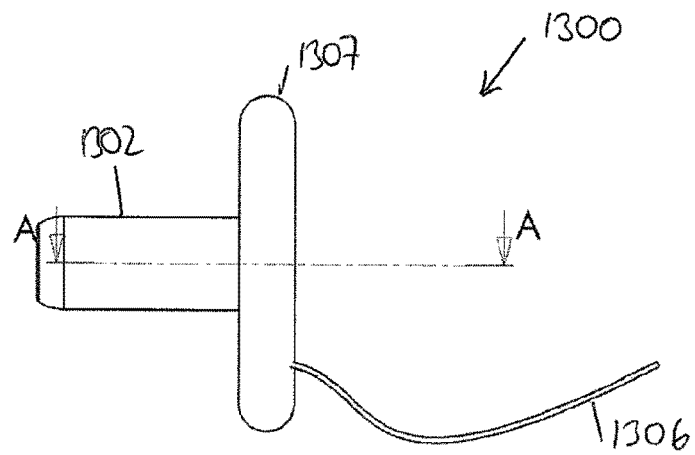
Figure 13C:
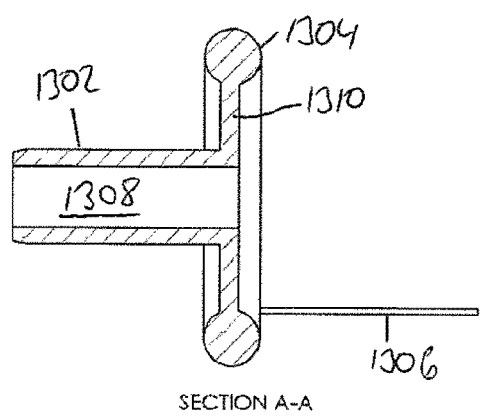

FIGS. 13A-13C show an adjustable incontinence device 1300, with a third anchoring/stabilizing section design, according to an exemplary embodiment of the invention.

FIG. 13 shows a simplified anchor 1320, optionally provided as an axially extending rod, attached along a central axis of a stiffenable/inflatable ring 1304, inflatable using a tube 1306. In alternative embodiments, the rod is coupled other than along the axis and/or is at an angle to ring 1304 other than perpendicular and/or is bent. In an alternative embodiment, tube 1306 is used for a wire-based stiffening mechanism, whereby a wire internal to ring 1304 is retracted relative to tube 1306 and thereby stiffen ring 1304.

As shown in FIG. 13C, apertures for allowing vaginal secretions flow may be provided, for example along rod 1302, as a lumen 1308, for example, if a membrane 1310 prevent other flow through ring 1304. FIG. 13C does not show an internal lumen of ring 1304. In some embodiments, such a lumen is provided only along part of a circumference of the inflatable ring, for example, 20%, 30%, 40%, 60%, 90% or intermediate amounts. While partial inflation may reduce the orientation-insensitivity of the ring, this may be useful for rings where it is desired to apply additional pressure at specific points.

Optionally, membrane 1310 is soft enough so that when ring 1304 is uninflated, the device may be easily inserted and/or removed.

In an exemplary embodiment of the invention, this and other devices may be inserted using an applicator, for example, a tube with a plunger used to push out the device. Optionally, the plunger is a hollow tube and/or carries the tensioning mechanism and/or control therein.

In an exemplary embodiment of the invention, the device used and/or settings are selected according to one or more of pathology, comfort, vaginal size, vaginal irritation, activity level and/or caregiver convenience. In some cases, the useful settings are determined using a trial and error period. In some cases, eth optimal settings change over time and are tracked, for example, using a trial and error method.

Materials

In embodiments of the invention, anchor arms 310 are constructed of a flexible material. Examples of flexible materials suitable for use in embodiments of the invention include, but are not limited to, silicone, nylon and polyurethane. Materials useful in construction of ring 202 are described above. Fluids useful in adjusting tension of ring 202 are described above. Optionally, tensioning element can be constructed of a rigid material, for example PVC (polyvinylchloride), optionally with joints, whereby the joints are made stiffer by increased fluid pressure.

One consideration in material selection is a degree of disposability of the device (e.g., 200 or 300). In embodiments of the invention, the device is constructed to be durable through a single use, and then discarded. According to various embodiments of the invention, the single use can comprise a number of hours (e.g. 2, 4, 8, 12 or 24 hours or lesser or grater or intermediate numbers of hours) or a number of days (e.g. 1, 2, 4, 7, 14 or 21 days or lesser or greater or intermediate numbers of days). One production consideration is that, a cost of materials increases as the length of the single use increases. In embodiments of the invention, a single use device is provided as an individual sterile sealed unit (e.g. in a bag), optionally contained within an applicator. In embodiments of the invention, a device provided in an applicator is flaccid, so it does not "lose" memory of a correct shape as a regular elastic device might.

In other embodiments of the invention, the device is adapted for re-use. Optionally, the device is constructed to withstand repeated sterilization (e.g. by steam pressure, formaldehyde gas or UV irradiation or dry heat) and/or washing (e.g. with detergents and/or solvents). In embodiments of the invention, a degree of flexibility of materials is sufficiently high to permit insertion into the vagina and/or storage in an applicator, but not so high as to permit shifting of the device within the vagina.

It is expected that during the life of a patent maturing from this application many relevant urinary incontinence devices will be developed and the scope of the term urinary incontinence device is intended to include all such new technologies a priori. As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. An apparatus for amelioration of urinary incontinence in a female subject, the apparatus comprising:
   (a) a ring with adjustable stiffness, adapted for intra-vaginal insertion, wherein said ring comprises an inner lumen in fluid communication with a tensioning extension and wherein said tensioning extension comprises:
      (i) a reservoir of material, and
      (ii) a transfer element adapted to move at least a portion of the material into said inner lumen of said ring, wherein the transfer element comprises a constricting element axially translatable along said reservoir;
   (b) a stabilizing projection comprising an anchor configured to extend in one direction axially towards a cervix of the female subject and away from said ring, said anchor sized for one or more of reducing translational motion, reducing tipping of the ring and/or reducing ring rotation, with respect to a vaginal wall by extending away from the ring, said stabilizing projection having a size, shape, stiffness and position configured to stabilize said ring within the vagina; and,
   (c) wherein said tensioning extension is adapted to extend outside of a body of the female subject, said tensioning extension adapted for selectively increasing and decreasing a rigidity of said ring after insertion thereof.

2. The apparatus according to claim 1, wherein said ring is adapted to switch from a first geometric configuration outside the body to a second configuration after intra vaginal insertion.

3. The apparatus according to claim 2, wherein said switch from said first configuration to said second configuration is performed mechanically.

4. The apparatus according to claim 1, wherein said apparatus includes a stiffening control.

5. The apparatus according to claim 1, wherein said material comprises a liquid.

6. The apparatus according to claim 1, wherein said material comprises a gas.

7. The apparatus according to claim 1, wherein said reservoir of material comprises an additional length of tubing defining a lumen in fluid communication with said inner lumen of said ring.

8. The apparatus according to claim 1, wherein said tensioning extension comprises a plurality of at least 3 different stable states corresponding to different stiffness states of said ring.

9. The apparatus according to claim 1, comprising at least one transverse support element engaging said ring.

\* \* \* \* \*